(12) United States Patent
Choi et al.

(10) Patent No.: US 7,678,390 B2
(45) Date of Patent: Mar. 16, 2010

(54) CARBON MONOXIDE AS A BIOMARKER AND THERAPEUTIC AGENT

(75) Inventors: Augustine M. K. Choi, Pittsburgh, PA (US); Leo E. Otterbein, New Kensington, PA (US)

(73) Assignees: Yale University, New Haven, CT (US); John Hopkins University, Baltimore, MD (US)

( * ) Notice: Subject to any disclaimer, the term of this patent is extended or adjusted under 35 U.S.C. 154(b) by 0 days.

(21) Appl. No.: 10/053,535

(22) Filed: Jan. 15, 2002

(65) Prior Publication Data

US 2002/0155166 A1    Oct. 24, 2002

Related U.S. Application Data

(63) Continuation of application No. 09/538,788, filed on Mar. 30, 2000, now abandoned.

(60) Provisional application No. 60/127,616, filed on Apr. 1, 1999.

(51) Int. Cl.
A61K 33/00 (2006.01)
A61P 1/00 (2006.01)

(52) U.S. Cl. .................................................. 424/699

(58) Field of Classification Search ................ 424/699, 424/718, 613
See application file for complete search history.

(56) References Cited

U.S. PATENT DOCUMENTS

| | | | |
|---|---|---|---|
| 4,053,590 A | 10/1977 | Bonsen et al. | |
| 4,264,739 A | 4/1981 | Grabner et al. | |
| 4,923,817 A | 5/1990 | Mundt | |
| 5,084,380 A | 1/1992 | Carney | |
| 5,180,366 A | 1/1993 | Woods | 604/96.01 |
| 5,240,912 A | 8/1993 | Todaro | |
| 5,293,875 A | 3/1994 | Stone | |
| 5,449,665 A | 9/1995 | Solevi | 514/46 |
| 5,476,764 A | 12/1995 | Bitensky | |
| 5,498,421 A | 3/1996 | Grinstaff et al. | |
| 5,632,162 A | 5/1997 | Billy | |
| 5,664,563 A | 9/1997 | Schroeder et al. | |
| 5,731,326 A | 3/1998 | Hart et al. | |
| 5,763,431 A | 6/1998 | Jackson | |
| 5,792,325 A | 8/1998 | Richardson | 204/164 |
| 5,882,674 A | 3/1999 | Herrmann et al. | |
| 5,885,621 A | 3/1999 | Head et al. | |
| 5,914,316 A | 6/1999 | Brown et al. | |
| 6,066,333 A | 5/2000 | Willis et al. | 424/464 |
| 6,069,132 A | 5/2000 | Revanker | |
| 6,203,991 B1 | 3/2001 | Nabel et al. | |
| 6,313,144 B1 | 11/2001 | McCullough et al. | |
| 6,316,403 B1 | 11/2001 | Pinsky et al. | |
| 7,045,140 B2 | 5/2006 | Motterlini et al. | |
| 7,238,469 B2 | 7/2007 | Bach et al. | |
| 2003/0009127 A1 | 1/2003 | Trescony et al. | |
| 2003/0064114 A1 | 4/2003 | Motterlini et al. | 424/646 |
| 2003/0068387 A1 | 4/2003 | Buelow et al. | |
| 2003/0219496 A1 | 11/2003 | Otterbein et al. | |
| 2003/0219497 A1 | 11/2003 | Otterbein et al. | |
| 2004/0005367 A1 | 1/2004 | Otterbein et al. | |
| 2004/0052866 A1 | 3/2004 | Otterbein et al. | |
| 2004/0067261 A1 | 4/2004 | Haas et al. | |
| 2004/0131703 A1 | 7/2004 | Bach et al. | |
| 2004/0197271 A1 | 10/2004 | Kunka et al. | |
| 2004/0228930 A1 | 11/2004 | Billiar et al. | |
| 2004/0258772 A1 | 12/2004 | Otterbein et al. | |
| 2005/0048133 A1 | 3/2005 | Pinsky et al. | |
| 2005/0215468 A1 | 9/2005 | Bar-Or et al. | |
| 2005/0250688 A1 | 11/2005 | Pinsky et al. | |
| 2006/0003922 A1 | 1/2006 | Bach et al. | |
| 2007/0202083 A1 | 8/2007 | Bach et al. | |

FOREIGN PATENT DOCUMENTS

| | | |
|---|---|---|
| FR | 2 816 212 | 5/2002 |
| WO | WO 94/22482 | 10/1994 |
| WO | WO 95/35105 | 12/1995 |
| WO | WO 98/08523 | * 3/1998 |
| WO | WO 98/13058 | 4/1998 |
| WO | WO 99/47512 | 9/1999 |

(Continued)

OTHER PUBLICATIONS

STN/CAS online, file BIOSIS, Acc. No. 1996:420959, Doc. No. PREV199699143315 (Choi et al., American Journal of Respiratory Cell and Molecular Biology (1996), vol. 15, No. 1, pp. 9-19), Abstract.*

STN/CAS online, file SCISEARCH, Acc. No. 94:51937, Doc. No. MP819 (Lefer et al., Methods and Findings in Experimental and Clinical Pharmacology (1993), vol. 15, No. 9, pp. 617-622), Abstract.*

(Continued)

*Primary Examiner*—Johann R Richter
*Assistant Examiner*—Frank I Cho
(74) *Attorney, Agent, or Firm*—Fish & Richardson P.C.

(57) ABSTRACT

The present invention relates to the use of carbon monoxide (CO) as a biomarker and therapeutic agent of heart, lung, liver, spleen, brain, skin and kidney diseases and other conditions and disease states including, for example, asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism. CO may be used to provide anti-inflammatory relief in patients suffering from oxidative stress and other conditions especially including sepsis and septic shock. In addition, carbon monoxide may be used as a biomarker or therapeutic agent for reducing respiratory distress in lung transplant patients and to reduce or inhibit oxidative stress and inflammation in transplant patients.

79 Claims, 10 Drawing Sheets

FOREIGN PATENT DOCUMENTS

| WO | WO 99/49880 | 10/1999 |
|---|---|---|
| WO | WO 02/09731 | 2/2002 |
| WO | WO 02/078684 | 10/2002 |
| WO | WO 02/092075 | 11/2002 |
| WO | 02/19687 | 1/2003 |
| WO | WO 03/000114 | 1/2003 |
| WO | WO 03/072024 | 9/2003 |
| WO | WO 03/088923 | 10/2003 |
| WO | WO 03/088981 | 10/2003 |
| WO | WO 03/096977 | 11/2003 |
| WO | WO 03/103585 | 12/2003 |
| WO | WO 2004/000368 | 12/2003 |
| WO | WO 2004/004817 | 1/2004 |
| WO | WO 2004/043341 | 5/2004 |
| WO | WO 03/094932 | 11/2007 |

OTHER PUBLICATIONS

STN/CAS online, file NIOSHTIC, Acc. No. 1997:109846, Doc. No. NIOSH-00153659 (Abidin et al., Kosmicheskaya Biologiya i Aviakosmicheskaya Meditsina (1978), No. 6, pp. 63-67), Abstract.*
STN/CAS online, file DRUGU, Acc. No. 1999-19188 (Vassalli et al., Eur. Resp. J. (1998), 12, Suppl. 28, 237s), Abstract.*
STN/CAS online, file NIOSHTIC, Acc. No. 1997:89614, Doc. No. NIOSH-00129570 (Stephens, Medical Press and Circular, vol. 183, pp. 283-288), Abstract.*
STN/CAS online, file EMBASE, Acc. No. 95184391, Doc. No. 1995184391 (Schipper et al., Annals of Neurology (1995) vol. 37, No. 6, pp. 758-768), Abstract.*
STN/CAS online, file NIOSHTIC, Acc. No. 1997:33870, Doc. No. NIOSH-00045743 (Ringel et al., Journal of the Neurological Sciences (1972), vol. 16, pp. 245-251), Abstract.*
STN/CAS online, file SCISEARCH, Acc. No. 1999: 859472 (Chapman et al., American Journal of Respiratory and Critical Care Medicine (Mar. 1999), vol. 159, No. 3, Supp., pp. A218-A218), Abstract.*
STN/CAS online, file NIOSHTIC, Acc. No. 1997:18892, Doc. No. NIOSH-00026382 (Campbell, British Journal of Experimental Pathology, vol. 15, No. 5, pp. 287-294 (1934)), Abstract.*
STN/CAS online, file CAPLUS, Acc. No. 1934:171114, Doc. No. 28:17114 (Maxwell et al., J. Pharmacol., vol. 49, pp. 270-282 (1933)), Abstract.*
Wing-Gaia et al., International Journal of Sport Nutrition and Exercise Metabolism (2005), vol. 15, pp. 680-688.*
Cantrell et al., "Low-Dose Carbon Monoxide Does Not Reduce Vasoconstriction in Isolated Rat 22 Lungs", *Experimental Lung Research* 22:21-32, 1996.
Cardell et al., "Bronchodilation in vivo by carbon monoxide, a cyclic GMP related messenger", *British Journal of Pharmacology* 124:1065-1068, 1998.
Cecil Textbook of Medicine (21$^{st}$ Ed. 2000), vol. 1, pp. 273-279, 357-372, 387-419, 425-427, 436-448, 466-475, 507-512, 1060-1074.
Cecil Textbook of Medicine (21$^{st}$ Ed. 2000), vol. 2, pp. 1492-1499, 2042-2047, 2079-2081.
Friebe et al., "YC-1 Potentiates Nitric Oxide- and Carbon Monoxide-Induced Cyclic GMP Effects in Human Platelets", *Molecular Pharmacology* 54(6)962-967, 1998.
Grau et al., "Influence of Carboxyhemoglobin Level on Tumor Growth, Blood Flow, and Radiation Response in an Experimental Model", *Int. J. Radiation Oncology Biol. Phys.* 22:421-424, 1992.
The Merck Manual (16$^{th}$ ed. 1992), pp. 646-657.
The New Encyclopedia Britannica (15$^{th}$ ed. 1994), vol. 26, Macropaedia, p. 756.
Otterbein et al., "Carbon Monoxide has Anti-Inflammatory Effects Involving the Mitogen-Activated Protein Kinase Pathway", *Nature Medicine* 6(4):1-7, 2000.
Otterbein et al., "Carbon Monoxide Provides Protection Against Hyperoxic Lung Injury", *The American Physiological Society*, L688-L694, 1999.
Siow et al., "Heme oxygenase-carbon monoxide signaling pathway in atherosclerosis: anti-atherogenic actions of bilirubin and carbon monoxide?" *Cardiovascular Research* 41:385-394, 1999.

SRN/CAS online, file EMBASE, Acc. No. 95184391, Doc. No. 1995184391, (Schipper et al., "Expression of heme oxygenase-1 in the senescent and Alzheimer-diseased brain", Annals of Neurology (1995), vol. 37, No. 6, 758-768), Abstract.
Yuan et al., "Evidence of increased endogenous carbon monoxide production in newborn rat endotoxicosis," Chinese Medical Sciences Journal (1997), vol. 12, No. 4, 212-215.
Arita et al., "Prevention of Primary Islet Isograft Nonfunction in Mice with Pravastatin," *Transplantation*, 65:1429-33, 1998.
Arnush et al., "IL-1 Produced and Released Endogenously within Human Islets Inhibits β Cell Function," J. Clin Invest. 702:516-26, 1998.
Bach et al., "Accommodation of vascularized xenografts: Expression of "protective genes" by donor endothelial cells in a host Th2 cytokine environment," *Nature Med.* 3:196-202,1997.
Berney et al., "Islet cell transplantation: the future?" *Langenbechs Arch. Surg.* 385: 378-8, 2000.
Bentley et al., "Successful cardiac transplantation with methanol or carbon monoxide-poisoned donors," *Thorac Surg* (2001), Apr.; 71(4):1194-7.
Brouard et al., "Carbon monoxide generated by heme oxygenase-1 suppresses endothelial cell apoptosis," *J Exp Med* (2000), Oct. 2; 192(7):1015-26.
Carlsson et al., "Measurements of Oxygen Tension in Native and Transplanted Rat Pancreatic Islets," *Diabetes* 47:1027-32, 1998.
Christodoulides et al., "Vascular Smooth Muscle Cell Heme Oxygenases Generate Guanylyl Cyclase-Stimulatory Carbon Monoxide," *Circulation* 97:2306-9, 1995.
Corbett et al., "Nitric oxide mediates cytokine-induced inhibition of insulin secretion by human islets of Langerhans," *Proc. Natl. Acad. Sci USA* 90:1731-5, 1993.
Gaine et al., "Introduction of heme oxygenase-1 with hemoglobin depresses vasoreactivity in rat aorta," *Vasc Res* (1999), Mar.-Apr.; 36(2):114-9.
Grau et al., "Influence of Carboxyhemoglobin Level on Tumor Growth, Blood Flow, and Radiation Response in an Experimental Model," *Int. J. Radiation Oncology Biol. Phys.* 22:421-424, 1992.
Hantson et al., "Organ transplantation from victims of carbon monoxide poisoning," *Ann Emerg Med* (1996), May; 27(5):673-4.
Hebert et al., "Transplantation of kidneys from a donor with carbon monoxide poisoning," New Engl J Med (1992), Jun. 4; 326(23):1571.
Iberer et al., "Cardiac allograft harvesting after carbon monoxide poisoning. Report of a sucessful orthotopic heart transplantation," *J Heart Lung Transplant* (1993), May-Jun; 12(3):499-500.
Kaufman et al., "Differential Roles of Mac-1$^+$ Cells, and CD4$^+$ and CD8$^+$ T Lymphocytes in Primary Nonfunction and Classic Rejection of Islet Allografts," *J Exp Med.* 772:291-302, 1990.
Koerner et al., "Extended donor criteria: use of cardiac allografts after carbon monoxide poisoning," *Transplantation* (1997), May 15; 63(9):1358-60.
Lacy et al., "Transplantation of Pancreatic Islets," *Annu. Rev. Immunol.*, 2:183-98, 1984.
Leikin et al., "The toxic patient as a potential organ donor," *Am J Emerg Med* (1994), Mar.; 12(2):151-4.
Mandrup-Poulsen et al., "Human Tumor Necrosis Factor Potentiates Human Interleukin 1-Mediated Rat Pancreatic β-Cell Cytotoxicity," *J. Immunol.* 739:4077-82, 1987.
Mansouri et al., "Alteration of Platelet Aggregation by Cigarette Smoke and Carbon Monoxide," *Thromb Haemost.* 48:286-8, 1982.
Myers, "Cirrhotic cardiomyopathy and liver transplantation," *Liver Transpl* (2000), Jul.; 6(4 Suppl 1):S44-52. Review.
Nagata et al.,"Destruction of Islet Isografts by Severe Nonspecific Inflammation," *Transplant Proc.* 22:855-6, 1990.
Petrache et al., "Heme oxygenase-1 inhibits TNF-α-induced apoptosis in cultured fibroblasts," *Am. J. Physiol. Lung Cell Mol. Physiol.* 287: L312-L319, 2000.
Pozzoli et al., "Carbon Monoxide as a Novel Neuroendocrine Modulator: Inhibition of Stimulated Corticotropin-Releasing Hormone Release from Acute Rat Hypothalamic Explants," *Endocrinology* 735:2314-2317, 1994.
Rabinovitch et al., "Transfection of Human Pancreatic Islets With an Anti-Apoptotic Gene (*bcl-2*) Protects β-Cells From Cytokine-Induced Destruction," *Diabetes* 48:1223-9, 1999.

Roberts et al., "Successful heart transplantation from a victim of carbon monoxide poisoning," *Ann Emerg Med* (1995), Nov.; 26(5):652-5.

Sato et al., "Carbon monoxide generated by heme oxygenase-1 suppresses the rejection of mouse to rat cardiac transplants," *J. Immunol.* 166: 4185-4194 (2001).

Shapiro et al., "Islet Transplantation in Seven Patients with Type 1 Diabetes Mellitus Using a Glucocorticoid-Free Immunosuppressive Regimen," *N. Engl. J. Med.*, 343:230-8, 2000.

Shennib et al., "Successful transplantation of a lung allograft from a carbon monoxide-poisoning victim," *Heart Lung Transplant* (1992), Jan.-Feb.; 11(1 Pt 1): 68-71.

Smith et al., "Successful heart transplantation with cardiac allografts exposed to carbon monoxide poisoning," *Heart Lung Transplant* (1992), Jul.-Aug.; 11(4 Pt. 1):698-700.

Soares et al., "Expression of heme oxygenase-1 can determine cardiac xenograft survival," *Nat Med.* 4:1073-1077, 1998.

Tenderich et al., "Hemodynamic follow-up of cardiac allografts from poisoned donors," *Transplantation* (1998), Nov. 15; 66(9): 1163-7.

Tenhunen et al., "The Enzymatic Conversion of Heme to Bilirubin by Microsomal Heme Oxygenase," *Proc Natl Acad Sci USA* 61:748-755, 1968.

Utz et al., "Carbon Monoxide Relaxes Ileal Smooth Muscle Through Activation of Guanylate Cyclase," *Biochem Pharmacol.* 47:195-201, 1991.

Verma et al., "Carbon Monoxide: A Putative Neural Messenger," *Science* 259:381-384, 1993.

Verran et al., "Use of liver allografts from carbon monoxide poisoned cadaveric donors," *Transplantation* (1996), Nov. 27; 62(10):1514-5.

Weir et al., "Scientific and Political Impediments to Successful Islet Transplantation," *Diabetes* 46:1247-56, 1997.

Weir et al., "Islet Transplantation as a treatment for diabetes," *J. Am. Optom. Assoc.* 69:727-32, 2000.

Yuan et al., "Evidence of increased endogenous carbon monoxide production in newborn rat endotoxicosis," *Chinese Medical Sciences Journal* (1997), vol. 12, No. 4, 212-215.

Campbell, "Cancer of Skin and Increase in Incidence of Primary Tumours of Lung in Mice Exposed to Dust Obtained from Tarred Roads," *British Journal of Experimental Pathology*, vol. 15, No. 5, pp. 287-294 (1934).

Campbell, "Living at Very High Altitudes and Maintenance of Normal Health," *Lancet*, 1:370 (1930).

Campbell, "The Effect of Carbon Monoxide and Other Agents Upon the Rate of Tumour Growth," *J. Path. Bact.*, 35:379 (1933).

Chapman et al., "Exogenous Carbon Monoxide Attenuates Aeroallergen-Induced Eosinophilic Inflammation in Mice,"*American Journal of Respiratory and Critical Care Medicine* (Mar. 1999), vol. 159, No. 3, Supp., pp. A218.

Hayes, "A Review of Modern Concepts of Healing of Cutaneous Wounds," *J. Dematol. Surg. Oncol.* 3:2 Mar./Apr. 1977, 188-193.

Maxwell et al., "Studies in Cancer Chemotherapy, XI. The Effect of CO, HCN and Pituitrin upon Tumor Growth," *J. Pharmacol.*, vol. 49, pp. 270-282 (1933).

Otterbein et al., "Carbon Monoxide Provides Protection Against Hyperoxic Lung Injury in Rats," *American Journal of Respiratory and Critical Care Medicine* (Mar. 1999), vol. 159, No. 3, Supp., pp. A218.

Peek et al., "Extracorporeal Membrane Oxygenation for Adult Respiratory Failure," *Chest*, 112:3, Sep. 1997 759-764.

Taylor, "Anti-TNF Therapy for Rheumatoid Arthritis and Other Inflammatory Diseases," *Molecular Biotechnology*, vol. 19, 2001 p. 153-168.

Katori, et al., "Heme oxygenase-1 system in organ transplantation," *Transplantation*, vol. 74, No. 7, pp. 905-912 (2002).

Tulis, et al., "Adenovirus-mediated heme oxygenase-1 gene delivery inhibits injury-induced vascular neointima formation." *Circulation* 104 (22) 2710-5 (2001).

Singhal, et al., "Effects of normobaric hyperoxia in a rat model of focal cerebral ischemia-reperfusion." *Journal of Cerebral Blood Flow and Metabolism* 22 (7) 861-8 (2002).

Carraway, et al., "Induction of Ferritin and Heme Oxygenase-1 by Endotoxin in the Lung," *American Journal of Physiology-Lung Cellular and Molecular Physiology*, vol. 275, Issue 3, pp. L583-L592, Sep. 1998.

Otterbein, et al., "Mechanism of Hemoglobin-induced Protection against Endotoxemia in Rats: A Ferritin-independent Pathway," *American Journal of Physiology-Lung Cellular and Molecular Physiology*, vol. 272, Issue 2, pp. L268-L275, 1997.

Brown et al., "In vivo binding of carbon monoxide to cytochrome *c* oxidase in rat brain", American Physiological Society, pp. 604-610 (1990).

Chapman et al., "Carbon Monoxide Attenuates Aeroallergen-induced Inflammation in Mice",*Am. J. Physiol. Lung Cell Mol Physiol.* 281:L209-L216 (2001).

Davidson et al., "Inflammatory Modulation and Wound Repair"*J Investigative Dermatology* xi-xii (2003).

Dioum et al., "NPAS2: A Gas-Responsive Transcription Factor", Sciencexpress/www.sciencexpress.org/21_November_2002/pages_1-6/10.1126/science.1078456.

Donnelly et al., "Expression of Heme-Oxygenase in Human Airway Primary Epithelial Cells", *J Respiratory Critical Care Med* 159(3):A218 (1999).

Grau et al., "Effect of Carbon Monoxide Breathing on Hypoxia and Radiation Response in the SCCVII Tumor in vivo", *Int. J. Radiation Oncology Biol. Phys.* 29:449-454 (1994).

Lee et al., "Regulation of Heme Oxygenase-1 Expression in Vivo and in Vitro in Hyperoxic Lung Injury", *Am. J. Respir. Cell Biol.* 14:556-568 (1996).

Meilin et al., Effects of carbon monoxide on the brain may be mediated by nitric oxide, *J Appl Physiol.* 81(3):1078-83 (1996).

Minamino et al, "Targeted expression of heme oxygenase-1 prevents the pulmonary inflammatory and vascular responses to hypoxia", *PNAS* 98(15):8798-8803 (2001).

Paredi et al., "Increased Carbon Monoxide in Exhaled Air of Cystic Fibrosis Patients", *J Respiratory Critical Care Med* 159(3):A218 (1999).

Piantadosi et al., "Production of Hydroxyl Radical in the Hippocampus After CO Hypoxia Hypoxia in the Rat", *Free Radical Biol. & Med.* 22(4):725-732 (1997).

Tamayo et al., "Carbon monoxide inhibits hypoxic pulmonary vasoconstriction in rats by a cGMP-independent mechanism", *Pflugers Arch.* 434(6):698-704 (1997).

Wang et al., "Resurgence of carbon monoxide: an endogenous gaseous vasorelaxing factor", *Can. J. Physiol. Pharmacol.* 76:1-15 (1998).

Welty et al., "Hyperoxic Lung Injury is Potentiated by SPC-Promotor Driven Expression of an HO-1 Transgene in Mice", *J Respiratory Critical Care Med* 159(3):A218 (1999).

Weng et al., "Transpulmonary HO-1 Gene Delivery in Neonatal Mice", *J Respiratory Critical Care Med* 159(3):A218 (1999).

Favory et al., "Myocardial Dysfunction and Potential Cardiac Hypoxia in Rats Induced by Carbon Monxide Inhalation," Am. J. Respir. Crit. Care Med. 174:320-25 (2006).

"Carbon Monoxide Poisoning—Symptoms," http://my.webmd.com/hw/home_health/aa7304.asp, 1 page, retrieved Jul. 11, 2005.

"Carbon Monoxide Poisoning—What Happens," http://my.webmd.com/hw/home_health/aa7326.asp, 1 page, retrieved Jul. 11, 2005.

Choi, "Heme Oxygenase-1 Protects the Heart," Circulation Research 89:105-7 (2001).

Clayton et al., "Inhaled carbon monoxide and hyperoxic lung injury in rats," Am. J. Physiol. Lung Cell Mol. Physiol. 281:L949-57 (2001).

"Colorectal Cancer Treatment: an Overview," American Cancer Society, http://www.cancer.org, 2 pages (2000).

Farrugia et al., "Heme oxygenase, carbon monoxide, and interstitial cells of Cajal," Microscopy Res. and Technique 47:321-324 (1999).

Fujita et al., "Paradoxical rescue from ischemic lung injury by inhaled carbon monoxide driven by derepression of fibrinolysis," Nature Medicine 7:598-604 (2001).

Huizinga, "Physiology and pathophysiology of the interstitial cell of Cajal: from bench to bedside. II. Gastric motility: lessons from mutant mice on slow waves and innervation," Am. J. Physiol. Gastrointest. Liver Physiol. 281:G1129-34 (2001).

Kyokane et al., "Carbon Monoxide From Heme Catabolism Protects Against Hepatobiliary Dysfunction in Endotoxin-Treated Rat Liver," Gastroenterology 120:1227-40 (2001).

Lee et al., "Intestinal Motility and Absorption in Acute Carbon Monoxide Poisoning," Seoul J. Med. 15:95-105 (1974) (English translation provided).

Libby et al., "Chronic Rejection—Review," Immunity, 14:387-397 (2001).

Liu et al., "Carbon monoxide and nitric oxide suppress the hypoxic induction of vascular endothelial growth factor gene via the 5' enhancer," J. Biol. Chem. 273(24):15257-62 (1998).

Miller et al., "Heme oxygenase 2 is present in interstitial cell networks of the mouse small intestine," Gastroenterology 114:239-244 (1998).

Moore et al., "Inhaled Carbon Monoxide Suppresses the Development of Postoperative Ileus in the Murine Small Intestine," Gastroenterology, 124:377-391 (2003).

Moore et al., "Pre-treatrnent with Low Concentration of Carbon Monzide (250 to 75 ppm) for 3 hr prior to Laparotomy Protects Against Postoperative Ileus," Digestive Disease Week Abstracts and Itinerary Planner 2003: Abstract No. M1337 (2003).

Nachar at al., "Low-Dose Inhaled Carbon Monoxide Reduces Pulmonary Vascular Resistance During Acute Hypoxemia in Adult Sheep," High Altitude Medicine & Biology 2:377-385 (2001).

Nakao et al., "Immunomodulatory effects of inhaled carbon monoxide on rat syngeneic small bowel graft motility," Gut 52:1278-85 (2003).

Otterbein et al., "Carbon monoxide at low concentrations causes growth arrest and modulates tumor growth in mice," Am. J. Respir. Crit. Care Med. 163, Abstract A476 (2001).

Otterbein et al., "Carbon Monoxide suppresses arteriosclerotic lesions associated with chronic graft rejection and with balloon injury," Nature Medicine 9:183-90 (2003).

Pannen et al., "Protective Role of Endogenous Carbon Monoxide in Hepatic Microcirculatory Dysfunction after Hemorrhagic Shock in Rats," J. Clin. Invest. 102:1220-1228 (1998).

Suganuma et al., "A new process of cancer prevention mediated through inhibition of tumor necrosis factor alpha expression," Cancer Res. 56(16):3711-5 (1996).

Zhou et al., "Endogenous carbon monoxide and acute lung injury," Section of Respiratory System Foreign Medical Sciences 19:185-187 (1999) (English translation provided).

Zuckerbraun et al., "Carbon monoxide attenuated the development of necrotizing enterocolitis in an animal model," Surgical Infection Society 3:83, Abstract 71 (2002).

Zuckerbraun et al., "Carbon Monoxide Protects against Liver Failure through Nitric Oxide-induced Heme Oxygenase 1," J. Exp. Med., 198(11):1707-1716 (2003).

Appel et al., "The pig as a source of Cardiac xenografts," J. Card. Surg. 16:345-56 (2001).

Bach, "Heme oxygenase-1 as a protective gene," Wien. Klin. Wochenschr. 114(Suppl):4:1-3 (2002).

Billiar, "The diverging roles of carbon monoxide and nitric oxide in resuscitated hemorrhagic shock," Crit. Care Med. 27:2842-3 (1999).

Bracho et al., "Carbon Monoxide Protects against Organ Injury in Hemorrhagic Shock/Resuscitation," Journal of Surgical Research, 107:270, (2002), Abstract.

Brouard et al., "Carbon monoxide generated by Heme Oxygenase-1 (HO-1) suppresses endothelial cell apoptosis via activation of the p38 mitogen activated protein kinase (MAPK) pathway," Acta Haematologica 103(Suppl 1):64, (2000), Abstract.

Brouard et al., "Heme oxygenase-1 -derived carbon monoxide requires the activation of transcription factor NF-kappa B to protect endothelial cells from tumor necrosis factor-alpha-mediated apoptosis," J. Biol. Chem., 277(20):17950-17961, (2002).

Brouard et al., "Molecular mechanism underlying the anti-apoptotic effect of Heme oxygenase-1 derived carbon monoxide," Xenotransplantation, 8(Suppl 1): p. 22 (2001).

Calabrese et al., "Carbon Monoxide (CO) Prevents Apoptotic Events Related to Ischemia/Reperfusion (IR) Injury in an hDAF Pig-to-Primate Xenotransplantation Model," Xenotransplantation 10:488, (2003), Abstract.

Chapman and Choi, "Exhaled monoxides as a pulmonary function test: use of exhaled nitric oxide and carbon monoxide," Clin. Chest Med. 22:817-836 (2001).

Chin et al., "Transcriptional regulation of the HO-1 gene in cultured macrophages exposed to model airborne particulate matter," Am. J. Physiol. Lung Cell. Mol. Physiol., 284(3):L473-L480, (2003).

Choi and Otterbein, "Emerging role of carbon monoxide in physiologic and pathophysiologic states," Antioxid. Redox Signal. 4:227-228 (2002).

Cozzi et al., "Donor Preconditioning with Carbon Monoxide (CO) in Pig-to-Primate Xenotransplantation," Xenotransplantation 10:528, (2003), Abstract.

Crapo et al., "Single-breath carbon monoxide diffusing capacity," Clin. Chest Med., 22:637-649, (2001).

Deng et al., "Carbon Monoxide Potentiates Cerulein-Induced Pancreatitis in Chronic Alcohol-Fed Rats," Gastroenterology, 124(4):A618-19, (2003), Abstract.

Dyck et al., "Carbon Monoxide (CO) Attenuates Lipopolysaccharide (LPS)-Induced Cytokine Expression of IL-6," Acta Haematologica 103(Suppl 1):64, (2000), Abstract.

Günther et al., "Carbon monoxide protects pancreatic beta-cells from apoptosis and improves islet function/survival after transplantation," Diabetes, 51(4):994-999, (2002).

Hartsfield and Choi, "Mitogen activated protein kinase (MAPK) is modulated by both endogenous and exogenous carbon monoxide," FASEB Journal 12:A187, 1088, (1998), Abstract.

Hartsfield et al., "Differential signaling pathways of HO-1 gene expression in pulmonary and systemic vascular cells," Am. J. Physiol., 277(6 Pt 1):L1133-L1141, (1999).

Hartsfield et al., "Regulation of heme oxygenase-1 gene expression in vascular smooth muscle cells by nitric oxide," Am. J. Physiol., 273(5 Pt 1):L980-988, (1997).

Hartsfield, "Targeted Overexpression of Heme Oxygenase-1 (HO-1) Attenuates Hypoxia-Induced Right Ventricular Hypertrophy," FASEB Journal 13:A827, (1999), Abstract.

Horvath et al., "Haemoxygenase-1 induction and exhaled markers of oxidative stress in lung diseases', summary of the ERS Research Seminar in Budapest, Hungary, Sep. 1999," Eur. Respir. J., 18(2):420-430, (2001).

Kozma et al, "Role of carbon monoxide in heme-induced vasodilation," Eur. J. Pharmacol., 323:R1-2 (1997).

Moore et al., "Carbon Monoxide Protects against Intestinal Dysmotility Associated with Small Bowel Transplantation," Gastroenterology 122:A38, (2002), Abstract.

Moore et al., "Carbon Monoxide Suppresses the Development of Ileus Associated with Surgical Manipulation of the Small Intestine," Gastroenterology 122:A61-A62, (2002), Abstract.

Mori et al., "Evaluation of hypothermic heart preservation with University of Wisconsin solution in heterotopically and orthotopically transplanted canine hearts," J. Heart Lung Transplant. 13:688-950 (1994).

Morse et al., "Carbon monoxide-dependent signaling," Crit. Care Med., 30:S12-S17, (2001).

Morse et al., "Suppression of inflammatory cytokine production by carbon monoxide involves the JNK pathway and AP-1," J. Biol. Chem., 278(39):36993-36998, (2003).

Nakao et al., "Protective effect of carbon monoxide inhalation for cold-preserved small intestinal grafts," Surgery, 134:285-92, (2003).

Ning et al., "TGF-betal stimulates HO-1 via the p38 mitogen-activated protein kinase in A549 pulmonary epithelial cells," Am. J. Physiol. Lung Cell. Mol. Physiol., 283(5):L1094-L1102, (2002).

Otterbein et al., "Carbon Monoxide Inhibits TNFα-Induced Apoptosis and Cell Growth in Mouse Fibroblasts," American Journal of Respiratory and Critical Care Medicine 159(3 Suppl.):A285 (1999).

Otterbein et al., "Carbon Monoxide Modulates Lipolysaccharide (LPS)-Induced Inflammatory Responses in vivo and in vitro," American Journal of Respiratory and Critical Care Medicine 159(3 Suppl.): A481 (1999).

Otterbein et al., "Carbon Monoxide, A Gaseous Molecule with Anti-Inflammatory Properties," pp. 133-156 in *Disease Markers in Exhaled Breath*, Marczin et al., eds., Marcel Dekker, Inc., New York, (2003).

Otterbein et al., "Carbon Monoxide Mediates Anti-Inflammatory Effects Via the P38 Mitogen Activated Protein Kinase Pathway," Acta Haematologica 103: 64, (2000), Abstract.

Otterbein et al., "Carbon Monoxide Protects Against Oxidant-Induced Lung Injury in Mice Via the p38 Mitogen Activated Protein Kinase Pathway," Acta Haematologica 103:83, (2000), Abstract.

Otterbein et al., "Exogenous administration of heme oxygenase-1 by gene transfer provides protection against hyperoxia-induced lung injury," J. Clin. Invest., 103(7):1047-1054, (1999).

Otterbein et al., "Heme oxygenase: colors of defense against cellular stress," Am. J. Physiol. Lung Cell. Mol. Physiol., 279(6):L1029-L1037, (2000).

Otterbein et al., "Protective effects of heme oxygenase-1 in acute lung injury," Chest. 116:61S-63S, (1999).

Otterbein, "Anti-Inflammatory Effects of Carbon Monoxide in the Lung," Crisp Data Base National Institute of Health; Doc. No. CRISP/2003HL071797-01A1, (2003).

Pileggi et al., "Heme oxygenase-1 induction in islet cells results in protection from apoptosis and improved in vivo function after transplantation," Diabetes, 50(9):1983-1991, (2001).

Ryter and Choi, "Heme Oxygenase-1: Molecular Mechanisms of Gene Expression in Oxygen-Related Stress," Antioxid. Redox Signal. 4:625-632, (2002).

Ryter et al. "Heme oxygenase/carbon monoxide signaling pathways: Regulation and functional significance," Mol. Cell. Biochem., 234-235(1-2):249-63, (2002).

Ryter et al., "Mitogen Activated Protein Kinase (MAPK) Pathway Regulates Heme Oxygenase-1 Gene Expression by Hypoxia in Vascular Cells," Exp. Biol. Med., 228(5):607, (2003), Abstract.

Sarady et al., "Carbon monoxide modulates endotoxin-induced production of granulocyte macrophage colony-stimulating factor in macrophages," Am. J. Respir. Cell. Mol. Biol., 27(6):739-745, (2002).

Sarady et al., "Cytoprotection by heme oxygenase/CO in the lung," in *Disease Markers in Exhaled Breath*, Marczin and Yacoub, eds., IOS Press, 346:73-78, (2002).

Sasidhar et al., "Exogenous Carbon Monoxide Attenuates Mitogen Activated Protein Kinase (MAPK) Activation in Rat Pulmonary Artery Endothelial Cells Exposed to Hypoxia," American Journal of Respiratory and Critical Care Medicine. 1999;159(3 Suppl.):A352.

Sass et al., "Heme Oxygenase-1 Induction Prevents Apoptotic Liver Damage in Mice," Naunyn-Schmiedeberg's Archives of Pharmacology 367:R78, (2003).

Sethi et al, "Differential modulation by exogenous carbon monoxide of TNF-alpha stimulated mitogen-activated protein kinases in rat pulmonary artery endothelial cells," Antioxid. Redox Signal., 4:241-8, (2002).

Sethi et al., "Differential Effects of Exogenous Carbon Monoxide on TNF-α-Induced Mitogen Activated Protein (MAP) Kinase Signaling Pathway in Rat Pulmonary Artery Endothelial Cells," American Journal of Respiratory and Critical Care Medicine 159(3 Suppl.):A350 (1999).

Seyfried et al., "HO-1 induction protects mice from Immune-mediated liver injury," Naunyn-Schmiedeberg's Archives of Pharmacology 367:R80 (2003).

Slebos et al., "Heme oxygenase-1 and carbon monoxide in pulmonary medicine," Respir Res. 4(7):1-13, (2003).

Soares et al, "Heine oxygenase-1, a protective gene that prevents the rejection of transplanted organs," Immunol. Rev. 184:275-85, (2001).

Soares et al, "Modulation of endothelial cell apoptosis by heme oxygenase-1-derived carbon monoxide," Antioxid. Redox Signal., 4:321-329, (2002).

Soares et al., "Heme Oxygenase-1 and/or Carbon Monoxide can Promote Organ Graft Survival," in *Disease Markers in Exhaled Breath*, Marczin and Yacoub, eds., IOS Press, 346:267-273, (2002).

Song et al., "Carbon monoxide induces cytoprotection in rat orthotopic lung transplantation via anti-inflammatory and anti-apoptotic effects," Am. J. Pathol., 163(1):231-242, (2003).

Song et al., "Carbon monoxide inhibits human airway smooth muscle cell proliferation via mitogen-activated protein kinase pathway," Am. J. Respir. Cell. Mol. Biol. 27(5):603-610, (2002).

Song et al., "Regulation of IL-1beta-induced GM-CSF production in human airway smooth muscle cells by carbon monoxide," Am. J. Physiol. Lung Cell. Mol. Physiol., 284(1):L50-L56, (2003).

Stupfel and Bouley, "Physiological and Biochemical Effects on Rats and Mice Exposed to Small Concentrations of Carbon Monoxide for Long Periods," Ann. N.Y. Acad. Sci. 174:343-368 (1970).

Tobiasch et al, "Heme oxygenase-1 protects pancreatic β cells from apoptosis caused by various stimuli," J. Investig. Med., 49:566-71, (2001).

Yamashita et al., "Effects of HO-1 induction and carbon monoxide on cardiac transplantation in mice," Exp. Biol. Med., 228(5):616, (2003), Abstract.

Zhang et al., "Carbon monoxide inhibition of apoptosis during ischemia-reperfusion lung injury is dependent on the p38 mitogen-activated protein kinase pathway and involves caspase 3," J. Biol. Chem., 278(2):1248-1258, (2003).

Zhang et al., "Mitogen-activated protein kinases regulate HO-1 gene transcription after ischemia-reperfusion lung injury," Am. J. Physiol. Lung Cell. Mol. Physiol., 283(4):L815-L829, (2002).

Zuckerbraun and Billiar, "Heme oxygenase-1: a cellular Hercules" Hepatology, 37(4):742-744, (2003).

Zuckerbraun et al., "Carbon monoxide inhibits intestinal inducible nitric oxide synthase production and ameliorates intestinal inflammation in experimental NEC," J. Amer. College of Surgeons 197:S50 (2003).

Zuckerbraun et al., "Carbon Monoxide Protects Hepatocytes from TNF-alpha/Actinomycin D Induced Cell Death," Critical Care Medicine 29:A59 (2001).

Choi et al., "'Therapeutic' carbon monoxide may be a reality soon," Am. J. Respir. Crit. Care Med., 171(11):1318-1319 (2005).

Dolinay et al., "Can Inhalation Carbon Monoxide be utilized as a therapeutic modality in human diseases?", pp. 203-236 in *Breath Analysis for Clinical Diagnosis and Therapeutic Monitoring*, Amann and Smith, eds., World Scientific Publishing Company (2004).

Dolinay et al., "Inhaled carbon monoxide confers antiinflammatory effects against ventilator-induced lung injury," Am. J. Respir. Crit. Care Med. 170:613-20 (2004).

Mayr et al., "Effects of carbon monoxide inhalation during experimental endotoxemia in humans," Am. J. Respir. Crit. Care Med., 171:354-360 (2005).

Ryter et al., "Therapeutic applications of carbon monoxide in lung disease," Curr. Opin. Pharmacol., 6:257-262 (2006).

Ryter et al., "Heme oxygenase-1/carbon monoxide: from basic science to therapeutic applications," Physiol. Rev. 86(2):583-650 (2006).

Thom et al, "'Therapeutic' Carbon Monoxide May Be Toxic," Am. J. Respir. Crit. Care Med., 171(11):1318 (2005).

Otterbein, "Carbon monoxide: innovative anti-inflammatory properties of an age-old gas molecule," Antioxid. Redox Signal., 4:309-319 (2002).

Sato et al., "Carbon monoxide can fully substitute Heme Oxygenase-1 in suppressing the rejection of mouse to rat cardiac transplants," *Acta Haematologica*, 103(Suppl. 1):87, Abstract 348 (2000).

Sato et al, "Heme Oxygenase-1 or Carbon Monoxide Prevents the Inflammatory Response Associated with Xenograft Rejection," *Acta Haematologica*, 103(Suppl. 1):87, Abstract 345 (2000).

Toda et al., "Exogenous Carbon Monoxide Protects Endothelial Cells Against Oxidant Stress and Improves Graft Function After Lung Transplantation," *Circulation*, 98(17 Suppl.):I265, Abstract 1381 (1998).

Allred et al., "Effects of Carbon Monoxide on Myocardial Ischemia," Environmental Health Perspectives 91:89-132 (1991).

Arcasoy et al., "Erythropoietin (EPO) Stimulates Angiogenesis in Vivo and Promotes Wound Healing," Blood 98:822A-823A, Abstract (2001).

Caplan et al., "Role of asphyxia and feeding in a neonatal rat model of necrotizing enterocolitis," Pediatr. Pathol., 14:1017-1028 (1994).

Czlonkowska et al., "Immune processes in the pathogenesis of Parkinson's disease—a potential role for microglia and nitric oxide," Med. Sci. Monit. 8:RA165-RA177 (2002).

Goldberg and Schneider, "Similarities between the oxygen-sensing mechanisms regulating the expression of vascular endothelial growth factor and erythropoietin," J. Biol. Chem. 269:4355-359 (1994).

Guo, "The Research Status of the Gas Messenger Molecules of Nitric Oxide and Carbon Monoxide in the Biomedicine Field," Practical Journal of Cardiac, Cerebral and Pulmonary Vascular Diseases vol. 8(2) (2000) (English translation included).

Harmey and Bouchier-Hayes, "Vascular endothelial growth factor (VEGF), a survival factor for tumour cells: implications for anti-angiogenic therapy," Bioessays 24:280-83(2003).

Josko, "Vascular endothelial growth factor (VEGF) and its effect on angiogenesis," Medical Science Monitor 6:1047-52 (2000).

Krause et al., "Recombinant human erythropoietin and VEGF have equal angiogenic potency: Investigation in a novel in vitro assay of human vascular tissues," European Heart J. 22:154 Abstract (2001).

Mazzola et al., "Carbon monoxide pretreatment prevents respiratory derangement and ameliorates hyperacute endotoxic shock in pigs," FASEB J. 19:2045-2047 (2005).

Omaye, "Metabolic modulation of carbon monoxide toxicity," Toxicol. 180:139-150 (2002).

Potter et al., "The inflammation-induced pathological chaperones ACT and apo-E are necessary catalysts of Alzheimer amyloid formation," Neurobiology of Aging 22:923-30 (2001).

Shahin et al., "Carboxyhemoglobin in pediatric sepsis and the systematic inflammatory response syndrome," Clinical Intensive Care 11(6):311-17 (2000).

Stewart, "The effect of carbon monoxide on humans," J. Occup. Med. 18:304-309 (1976).

Stewart, "The effects of low concentrations of carbon monoxide in man," Scand. J. Respir. Dis. Suppl. 91:56-62 (1974).

Thiemermann, "Inhaled CO: deadly gas or novel therapeutic," Nature Medicine 7(5): 534-35 (2001).

Vreman et al., "Carbon monoxide and carboxyhemoglobin," Adv. Pediatr. 42:303-34 (1995).

Wright and Shephard, "Physiological effects of carbon monoxide," Int. Rev. Physiol. 20:311-68 (1979).

Zegdi et al., "Increased endogenous CO production in severe sepsis," Intensive Care Medicine 23:793-96 (2002).

Zuckerbraun et al., "Carbon monoxide protects against liver failure through nitric oxide-induced heme oxygenase 1," J Exp Med. 198(11):1707-16 (2003).

Bathoorn et al., "Effects of low dose inhaled carbon monoxide in patients with COPD," Eur. Respir. J., 28(Suppl.50):661s (2006).

Mazzola et al., "Carbon monoxide pretreatment prevents respiratory derangement and ameliorates hyperacute endotoxic shock in pigs," The FASB Journal [online], Oct. 13, 2005 [retrieved on Jun. 1, 2007]. Retrieved from the Internet:<URL:http://www.fasebj.org/cgi/doi/10.1096/fj.05-3782fje>.

American Thoracic Society, "Single breath carbon monoxide diffusing capacity (transfer factor): recommendations for a standard technique," Am. Rev. Respir. Dis. 136:1299-1307 (1987).

American Thoracic Society, "Single breath carbon monoxide diffusing capacity (transfer factor): recommendations for a standard technique-1995 update," Am. J. Respir. Crit. Care. Med. 152:2185-2198 (1995).

Bathoorn et al., "Anti-inflammatory effects of inhaled carbon monoxide in patients with COPD: a pilot study," Eur. Respir. J. 0: 09031936.00163206v1 (Aug. 22, 2007).

Bartholomew, G.W. and M. Alexander, "Microbial metabolism of carbon monoxide in culture and in soil," Appl. Environ. Microbiol., 37(5):932-937 (1979).

Bishop, G.A. et al., "Spontaneous acceptance of liver transplants in rodents: evidence that liver leucocytes induce recipient T-cell death by neglect," Immunol. Cell Biol., 80(1):93-100 (2002).

Datta, R. And J.G. Zeilcus, "Modulation of Acetone-Butanol-Ethanol Fermentation by Carbon Monoxide and Organic Acids," Appl. Environ. Microbiol., 49(3):522-529 (1985).

Kanoria, S. et al., "A model to study total hepatic ischemia-reperfusion injury," Transplant Proc., 36(9):2586-2589 (2004).

Medline Plus Medical Dictionary, definitions of organ, tissue and cell, accessed Oct. 9, 2007.

Baim and Grossman, "Treatment of Coronary Stenoses and Occlusions with Coronary Angioplasty," Harrison's Principles of Internal Medicine, 13th Ed., vol. 1, 193:986-987 (1994).

Carbon Monoxide to Prevent Lung Inflammation, http://www.clinicaltrials.gov/ct/show/NCT00094406?order=2 (website visited by applicant on Aug. 28, 2006).

Ellenhorn and Barceloux, "Carbon Monoxide" in Medical Toxicology, Diagnosis and Treatment of Human Poisoning, (New York, New York) pp. 820-829, (1988).

Hartsfield, "Cross talk between carbon monoxide and nitric oxide," Antioxid. Redox Signal. 4:301-307 (2002).

Johnson et al., "Relationships between drug activity in NCI preclinical in vitro and in vivo models and early clinical trials," Br. J. Cancer 84:1424-31 (2001).

Modification of Chronic Inflammation by Inhaled Carbon Monoxide in Patients with Stable Chronic Obstructive Pulmonary Disease (COPD). http://www.clinicaltrials.gov/ct/show/NCT00122694?order=1, website visited by Applicant on Aug. 28, 2006.

Morse and Choi, "Heme oxygenase-1: from bench to bedside," Am. J. Respir. Crit. Care Med. 172:660-670 (2005).

Motterlini et al., "Carbon Monoxide-Releasing Molecules: Characterization of Biochemical and Vascular Activities," Circ. Res. 90:e17-324 (2002).

Nakao et al., "A single intraperitoneal dose of carbon monoxide-saturated ringer's lactate solution ameliorates postoperative ileus in mice," J. Pharmacol. Exp. Ther. 319:1265-75 (2006).

Raman et al. "Inhaled carbon monoxide inhibits intimal hyperplasia and provides added benefit with nitric oxide," J. Vasc. Surg. 44:151-158 (2006).

Ramlawi et al., "Inhaled Carbon Monoxide Prevents Graft-Induced Intimal Hyperplasia in Swine," J. Surg. Res. 138:121-127 (2007).

Wang et al., "Carbon monoxide-induced vasorelaxation and the underlying mechanisms," Br. J. Pharmacol. 121:927-934 (1997).

Hanselmann et al., "Haem oxygenase-1: a novel player in cutaneous wound repair and psoriasis?" Biochem. J., 353:459-466 (2001).

Kimpara et al., "Microsatellite polymorphism in the human heme oxygenase-1 gene promoter and its application in association studies with Alzheimer and Parkinson disease," Hum. Genet., 100:145-147 (1997).

Lavrovsky et al., "Role of redox-regulated transcription factors in inflammation, aging and age-related diseases," Exp. Gerontol., 35:521-532 (2000).

Markesbery, "Oxidative stress hyopthesis in Alzheimer's disease," Free Radical Biol. Med., 1:134-147 (1997).

Soares et al., "Herne oxygenase-1: from biology to therapeutic potential," Trends Mol. Med., 15:50-58 (2009).

USPTO Final Office Action in U.S. Appl. No. 10/676,280, mailed Apr. 16, 2009, 17 pages.

USPTO Non-Final Office Action in U.S. Appl. No. 10/600,182, mailed Apr. 30, 2009, 10 pages.

* cited by examiner

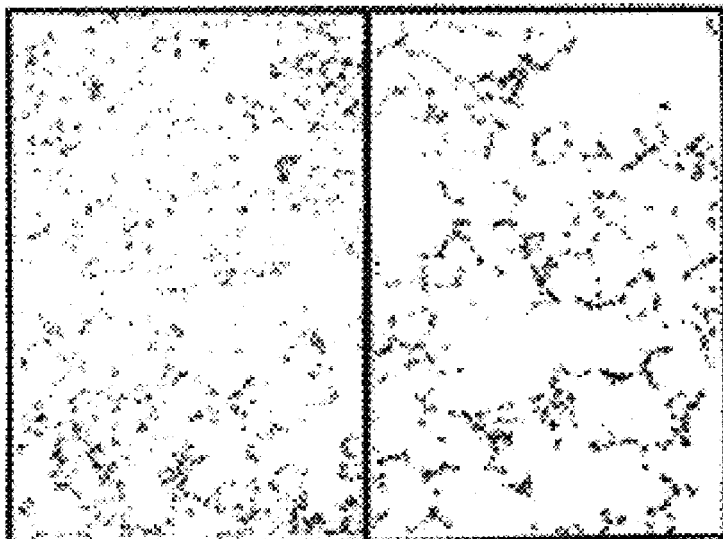
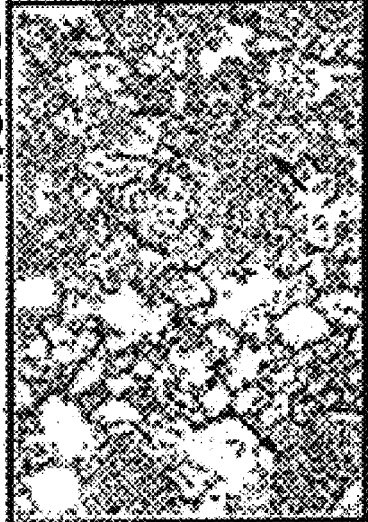
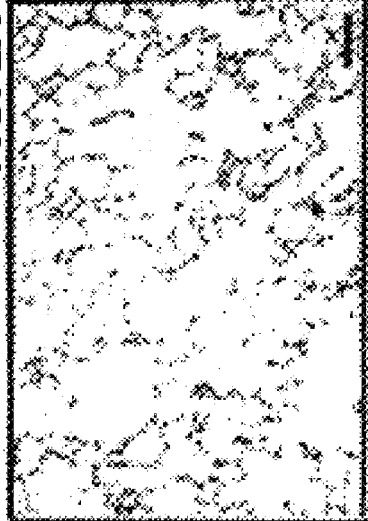
EFFECTS OF CO ON LUNG HISTOLOGY AFTER HYPEROXIA
FIG. 2A  FIG. 2B  FIG. 2C  FIG. 2D  FIG. 2E  FIG. 2F

EFFECTS OF CO ON LPS-INDUCED
MAPK ACTIVATION IN RAW 264.7 CELLS

ANALYSIS OF TNF-α EXPRESSION IN RAW 264.7 CELLS
FOLLOWING LPS IN THE PRESENCE AND ABSENCE OF CO

CARBON MONOXIDE AS A BIOMARKER AND THERAPEUTIC AGENT

RELATED APPLICATIONS

This application is a continuation of U.S. application Ser. No. 09/538,788, filed on Mar. 30, 2000, now abandoned, which claims priority from provisional application No. 60/127,616, filed Apr. 1, 1999.

STATEMENT AS TO FEDERALLY SPONSORED RESEARCH

This invention was made with Government support under National Institutes of Health (NIH) Grant Nos. HL60234, A142365, and HL55330. The Government has certain rights in this Invention.

FIELD OF THE INVENTION

The present invention relates to the use of carbon monoxide (CO) as a biomarker and therapeutic agent of heart, lung, liver, spleen, brain, skin and kidney diseases and other conditions and disease states including, for example, asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism. CO may be used to provide anti-inflammatory relief in patients suffering from oxidative stress and other conditions especially including sepsis and septic shock. In addition, CO may be used to store organs prior to transplantation. In addition, carbon monoxide may be used as a biomarker or therapeutic agent for reducing respiratory distress in lung transplant patients, to reduce or inhibit oxidative stress, inflammation or rejection of transplants in transplant patients.

BACKGROUND OF THE INVENTION

Heme oxygenase (HO) catalyzes the first and rate limiting step in the degradation of heme to yield equimolar quantities of biliverdin IXa, carbon monoxide (CO), and iron (Choi, et al., *Am. J. Respir. Cell Mol. Biol.* 15: 9-19; and Maines, *Annu. Rev. Pharmacol. Toxicol.* 37: 517-554). Three isoforms of HO exist; HO-1 is highly inducible while HO-2 and HO-3 are constitutively expressed (Choi, et al., supra, Maines, supra and McCoubrey, et al., *E. J. Bioch.* 247: 725-732). Although heme is the major substrate of HO-1, a variety of non-heme agents including heavy metals, cytokines, hormones, endotoxin and heat shock are also strong inducers of HO-1 expression (Choi, et al., supra, Maines, supra and Tenhunen, et al., *J. Lab. Clin. Med.* 75: 410-421). This diversity of HO-1 inducers has provided further support for the speculation that HO-1, besides its role in heme degradation, may also play a vital function in maintaining cellular homeostasis. Furthermore, HO-1 is highly induced by a variety of agents causing oxidative stress including hydrogen peroxide, glutathione depletors, UV irradiation, endotoxin and hyperoxia (Choi, et al., supra, Maines, supra and Keyse, et al., *Proc. Natl. Acad. Sci. USA.* 86: 99-103). One interpretation of this finding is that HO-1 can serve as a key biological molecule in the adaptation and/or defense against oxidative stress (Choi, et al., supra, Lee, et al., *Proc Natl Acad Sci USA* 93: 10393-10398; Otterbein, et al., *Am. J. J. Respir. Cell Mol. Biol.* 13: 595-601; Poss, et al., *Proc. Natl. Acad. Sci. USA.* 94: 10925-10930; Vile, et al., *Proc. Natl. Acad. Sci.* 91: 2607-2610; Abraham, et al., *Proc. Natl. Acad. Sci. USA.* 92: 6798-6802; and Vile and Tyrrell, *J. Biol. Chem.* 268: 14678-14681. Our laboratory and others have shown that induction of endogenous HO-1 provides protection both in vivo and in vitro against oxidative stress associated with hyperoxia and lipopolysaccharide-induced tissue injury (Lee, et al., supra, Otterbein, et al., supra and Taylor, et al., *Am. J. Physiol.* 18: L582-L591). We have also shown that exogenous administration of HO-1 via gene transfer can provide protection against oxidant tissue injury and elicit tolerance to hyperoxic stress (Otterbein, et al., *Am. J. Resp. Crit. Care Med.* 157: A565 (Abstr)).

Carbon monoxide (CO) is a gaseous molecule with known toxicity and lethality to living organisms (Haldane, *Biochem. J.* 21: 1068-1075; and Chance, et al., 1970, *Ann. NY Acad Sci.* 174: 193-204.). However, against this known paradigm of CO toxicity, there has been renewed interest in recent years in CO behaving as a regulatory molecule in cellular and biological processes based on several key observations. Mammalian cells have the ability to generate endogenous CO primarily through the catalysis of heme by the enzyme heme oxygenase (HO) (Choi, et al., supra and Maines, supra). The total cellular production of CO is generated primarily via heme degradation by HO (Marilena, *Biochem. Mol. Med.* 61: 136-142 and Verma, et al., 1993 *Science* 259: 381-384). Moreover, CO akin to the gaseous molecule nitric oxide, plays important roles in mediating neuronal transmission (Verma, et al., supra and Xhuo, et al., *Science* 260: 1946-1950) and in the regulation of vasomotor tone (Morita, and Kourembanas, 1995, *J. Clin. Invest.* 96: 2676-2682.; Morita, et al., 1995 *Proc. Natl. Acad. Sci. USA* 92:-1479; and Goda, et al., 1998, *J. Clin. Inv.* 101: 604-12). There is no data in the literature substantiating a protective role for CO in vivo against oxidative stress.

Septic shock and sepsis syndrome, resulting from excessive stimulation of immune cells, particularly monocytes and macrophages, remains one of the leading causes of death in hospitalized patients. Parillo, et al., *Ann. Intern. Med.* 113, 991-992 (1992). The pathophysiological alterations observed in sepsis are often not due to the infectious organism itself, but rather to the uncontrolled production of pro-inflammatory cytokines and chemokines including TNF-α, IL-1, and MIP-1 that leads to leukocyte recruitment, capillary leak and ultimately participates in the lethality of sepsis. Beutler, et al., 232, 977-980 (1986); Netea, et al., *Immunology* 94, 340-344 (1998); and Wolpe, et al., *J. Exp. Med.* 167, 570-581 (1988). Lipopolysaccharide (LPS), a constituent of the gram negative bacterial cell wall, is the leading cause of sepsis, and when administered experimentally to macrophages or mice, mimics the same inflammatory response. Following LPS administration, there is a rapid but transient increase in these pro-inflammatory mediators which are subsequently downmodulated by a battery of anti-inflammatory cytokines including interleukin-10 (IL-10) and interleukin-4 (IL-4), which inhibit the synthesis of the pro-inflammatory cytokines and chemokines. *J. Exp. Med.* 177, 1205-1208 (1993). LPS initially binds to the CD14 and toll-like receptor (TLR) 2 (or 4) at the cell surface, [Yang, et al., *Nature.* 395: 284-288 (1998) and Chow, et al., *J. Biol. Chem.* 274: 10689-10692 (1999)] and has then been shown to activate the mitogen activated protein (MAP) kinase pathways including p38, p42/p44 ERK and JNK (MAP) kinases. Liu, et al., *J. Immunol.* 153, 2642-2652 (1994); Hambleton, et al., *Proc. Natl. Acad. Sci. USA.* 93, 2274-2778 (1996); Han, et al., *J. Biol. Chem.* 268, 25009-25014 (1993); Han, et al., *Science* 265, 808-811

(1994); Sanghera, et al., *J. Immunol.* 156, 4457-4465 (1996), and Raingeaud, et al., *J. Biol. Chem.* 270, 7420-7426 (1995). The relationship between the activation of these signaling molecules, downstream cytokine expression, and physiologic function represents an active line of investigation.

The United States Government has provided support for research which led to the present invention under one or more of NIH grant numbers HL60234, A142365 and HL55330. Consequently, the government retains certain rights in the invention.

OBJECTS OF THE INVENTION

It is an object of the present invention to provide novel gaseous mixtures containing low concentrations of carbon monoxide which may be used as therapeutic compositions.

It is another object of the present invention to provide a method for treating oxidative stress in a patient.

It is another object of the present invention to provide a method for treating a number of diseases and conditions in which oxidative stress occurs or is secondary.

It is yet another object of the present invention to provide a method for using carbon monoxide as a biomarker to determine that a patient producing carbon monoxide is suffering from oxidative stress or a condition or disease state in which oxidative stress is implicated.

At least one or more of these and/or other objects of the present invention may be readily gleaned from a review of the description of the invention which follows.

BRIEF DESCRIPTION OF THE INVENTION

The present invention relates to novel pharmaceutical compositions for delivering to patients suffering from the effects of oxidative stress, the compositions comprising effective concentrations of carbon monoxide in a gaseous mixture comprising oxygen and optionally, nitrogen gas (as well as other minor optional gaseous components). An additional aspect of the present invention is directed to a method for delaying the onset of, inhibiting or alleviating the effects of oxidative stress, the method comprising delivering a therapeutic gas comprising carbon monoxide in an amount and for a time effective to delay the onset of, inhibit or alleviate the affects of oxidative stress in the patient. It has unexpectedly been discovered that the delivery of a therapeutic gas comprising low concentrations (i.e., concentrations ranging from about 1 ppb (part per billion) to about 3,000 ppm (preferably above about 0.1 ppm within this range) of the gas, preferably about 1 ppm to about 2,800 ppm, more preferably about 25 ppm to about 750 ppm, even more preferably about 50 ppm to about 500 ppm) of carbon monoxide is an extremely effective method for delaying the onset of, inhibiting or reversing the effects of oxidative stress in a patient. This is an unexpected result. It is noted here that in the method aspects of the present invention, an amount of carbon monoxide in the therapeutic gaseous composition which is in excess of 0.3% may sometimes be used, depending upon the condition or disease state to be treated.

Another aspect of the present invention is directed to the use of carbon monoxide as a biomarker for determining that a patient is suffering from oxidative stress and is at risk for or is suffering from a number of conditions or disease states which are secondary to or result in oxidative stress, for example, asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism, among others. The method comprises detecting carbon monoxide in a patient's breath to determine whether detectable levels of carbon monoxide occur in the breath. If detectable levels of carbon monoxide appear in the patient's breath, the patient may be diagnosed with oxidative stress or for being at risk for oxidative stress. The manifestations of oxidative stress may take the form of one or more of the above-referenced conditions or disease states. Appropriate therapeutic steps or other steps may be taken after such diagnosis to alleviate or treat the condition which is responsible for the oxidative stress in the patient.

Another aspect of the present invention relates to the finding that in certain patients, the administration of carbon monoxide in effective amounts to the patient may be used to induce HO-1 enzyme in the patient and prevent or limit oxidative stress in the patient, especially including oxidative stress caused by hyperoxia or sepsis. HO-1 enzyme is implicated in maintaining homeostasis in the cells of the patient.

Still another aspect of the present invention relates to the use of carbon monoxide to delay the onset of, inhibit or alleviate the effects of oxidative stress which occur in transplant patients, in particular, organ transplant patients, especially, but not exclusively lung transplant patients.

Another aspect of the present invention relates to a method for inhibiting the production of pro-inflammatory cytokines such as TNF-α, IL-1β, IL-6, MIP-1β and augmenting the production (expression) of the anti-inflammatory cytokine IL-10 and IL-4 in a patient comprising administering to the patient an effective amount of CO.

Still another aspect of the present invention relates to a method to preserve organs or tissue for transplants comprising adding to media in which the organs or tissue are stored a preservative effective amount or concentration of carbon monoxide. In this aspect of the present invention, the inclusion of carbon monoxide in effective amounts reduces, inhibits or alleviates the formation of reactive oxygen in the stored organ or tissue, thus extending the period in which organ transplants can be effectively stored without suffering oxidative damage.

Another aspect of the present invention relates to a method to prevent or reduce the likelihood of damage caused by oxidative stress associated with hyperoxia in a patient comprising administering an effective amount of carbon monoxide to a hyperoxic patient.

BRIEF DESCRIPTION OF THE DRAWINGS

FIG. 1A represents pleural effusion volume after hyperoxic exposure. FIG. 1B represents protein accumulation in bronchoalveolar lavage (BAL) samples. Data presented are the mean values for six rats in each case.

FIGS. 2A-2F show the histological analysis of rat lung after hyperoxia. Formalin-fized sections of rat lungs were stained with hemotoxylin and eosin.

DETAILED DESCRIPTION OF THE INVENTION

Figure 1A:
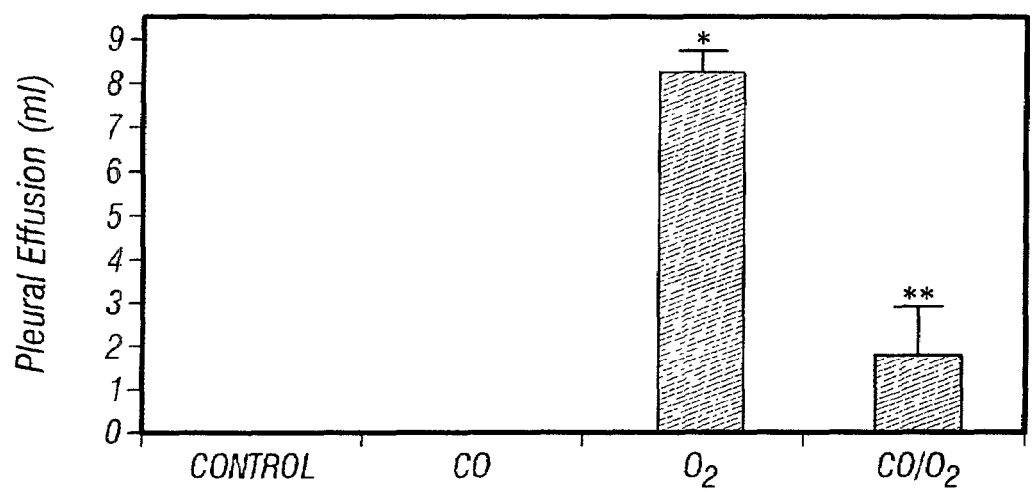
FIGS. 1A and 1B show the measurement of biological markers of lung injury after hyperoxia.

The following definitions are used to describe the present invention.

The term "carbon monoxide" or CO is used to describe molecular carbon monoxide in its gaseous state. In high concentrations and prior to the present invention, CO was understood to be poisonous and non-therapeutic, but useful in certain diagnostic tests at concentrations at or above 0.3%. Gaseous compositions according to the present invention comprise effective amounts of carbon monoxide which are less than 0.3% of the total weight of the composition and preferably less than about 0.28% by weight, even more preferably less than about 0.25% by weight carbon monoxide.

The term "oxidative stress" is used to describe a condition resulting from the overwhelming production of reactive oxygen which cannot be quenched by endogenous antioxidants. Oxidative stress may result in permanent tissue damage caused by the action of the reactive oxygen species on the tissue. The physiological manifestation of oxidative stress take the form of or occur during various conditions or disease states which include, asthma, emphysema, bronchitis, adult respiratory distress syndrome, sepsis or septic shock, cystic fibrosis, pneumonia, interstitial lung diseases, idiopathic pulmonary diseases, other lung diseases including primary pulmonary hypertension, secondary pulmonary hypertension, lung cancer and pulmonary vascular thrombotic diseases such as pulmonary embolism or any inflammatory disease of the lungs.

The term "sepsis" is used to describe the presence of various pus-forming and other pathogenic organisms or their toxins (generally, lipopolysaccharides or LPS bacterial cell walls) in the blood tissues. Sepsis will often result in oxidative stress in those tissues exposed to the pathogens or their toxins. Sepsis often manifests itself in the production of pro-inflammatory cytokines such as TNF-α, IL-1, IL-6 and MIP-1, the production of which is reduced or reversed by the administration of effective amounts of carbon monoxide.

The term "composition" or "carbon monoxide containing composition" is used throughout the specification to describe a gaseous composition which is administered to a patient to delay the onset of, inhibit or alleviate the effects of oxidative stress in a patient or to treat one or more of the conditions or disease states which manifest themselves or are secondary to oxidative stress. Compositions according to the present invention comprise 0% to about 79% by weight nitrogen, about 21% to about 100% by weight oxygen and about 0.0000001 to about 0.3% by weight (corresponding to about 1 ppb or 0.001 ppm to about 3,000 ppm, but preferably less than 3,000 ppm) carbon monoxide. More preferably, the amount of nitrogen in the gaseous composition comprises about 79% by weight, the amount of oxygen comprises about 21% by weight and the amount of carbon monoxide comprises about 0.0001% to about 0.25% by weight, preferably at least about 0.001% within this range, even more preferably about 0.005% to about 0.05% by weight of carbon monoxide.

The term "patient" is used throughout the specification to describe an animal, preferably a human, to whom treatment, including prophylactic treatment, with the carbon monoxide containing compositions according to the present invention is provided. For treatment of those infections, conditions or disease states which are specific for a specific animal such as a human patient, the term patient refers to that specific animal. In most applications of the present invention, the patient is a human. Veterinary applications, in certain indications, are clearly anticipated by the present invention.

The term "effective amount" shall mean the administration of carbon dioxide in an amount or concentration and for period of time including acute or chronic administration which is effective within the context of its administration for causing an intended effect or physiological outcome. Effective amounts of carbon monoxide for use in the present invention include amounts which are therapeutically effective for delaying the onset of, inhibiting or alleviating the affects of oxidative stress, treating one or more of the conditions or diseases which are secondary to or result in oxidative stress. An effective amount of carbon monoxide within the context of reducing the production or effect of inflammatory cytokines, for example, TNF-α, IL-1, IL-6 and MIP-1, among others and inducing or increasing the production of anti-inflammatory cytokines such as IL-10, among others. Within the context of transplant patients, an effective amount of carbon monoxide is that amount administered to the transplant patient to reduce the likelihood of rejection through an unfavorable immunological reaction. Within the context of preserving stored organs to be used for transplantation, an effective amount of carbon monoxide is that amount which is bubbled into the medium in which the transplant organs are stored in order to enhance preservation of the organ and reducing the likelihood that the organ will be subject to some measure of oxidative damage. Although effective amounts of CO generally fall within the range of about 0.1 ppm to about 3,000 ppm, amounts outside of these ranges, in certain instances, may be used, depending upon the final use of the composition.

The term "biomarker" is used to describe carbon monoxide which is produced in the breath of a patient in minor, detectable amounts which provides evidence that the patient is at risk for, in the early stages of or is suffering from oxidative stress and is at risk for or is suffering from one or more of the conditions or disease states which are secondary to or which may result in oxidative stress. The amount of carbon monoxide in the breath of a patient which may function as a biomarker may be as low as 0.001 ppm, but is generally at least about 0.1 ppm or higher.

The term "inflammation" is used to describe the fundamental pathological process consisting of a dynamic complex of cytologic and histologic reactions that occur in the affected blood vessels and adjacent tissues in response to an injury or abnormal stimulation caused by a physical, chemical or biologic agent, including the local reactions and resulting morphologic changes, the destruction or removal of the injurious material, and the responses that lead to repair and healing. The so-called cardinal signs of inflammation are redness, heat, swelling, pain and, in certain cases, inhibited or lost function. The redness and warmth result from an increased amount of blood in the affected tissue, which is usually congested; swelling ordinary occurs from the congestion and exudation; pressure on (or stretching of) nerve endings as well as changes in osmotic pressure and pH which may lead to significant pain; the disturbance in function may result in impairment in movement or the actual destruction of an anatomic part or organ. The term inflammation includes various types of inflammation such as acute, allergic, alterative (degenerative), atrophic, catarrhal (most frequently in the respiratory tract), croupous, fibrinopurulent, fibrinous, immune, hyperplastic or proliferative, subacute, serous and serofibrinous. Inflammation localized in the kidneys, liver, heart, skin, spleen, brain, kidney and pulmonary tract, especially the lungs, and that associated with sepsis or septic shock is favorably treated by the methods according to the present invention.

The term "cancer" is used throughout the present invention as a general term to describe any of various types of malignant neoplasms, most of which invade surrounding tissues, may metastasize to several sites and are likely to recur after attempted removal and to cause death of the patient unless adequately treated. Cancers which may be treated using the present compositions and methods include, for example, stomach, colon, rectal, liver, pancreatic, lung, breast, cervix uteri, corpus uteri, ovary, prostate, testis, bladder, renal, brain/cns, head and neck, throat, Hodgkins disease, non-Hodgkins leukemia, skin melanoma, various sarcomas, small cell lung cancer, choriocarcinoma, mouth/pharynx, oesophagus, larynx, melanoma, kidney and lymphoma, among others.

Thus, according to an aspect of the present invention, a patient suspected of being in oxidative stress or at risk for oxidative stress is monitored to determine whether detectable levels of carbon monoxide may be measured in the exhaled breath of the patient. If detectable levels of carbon monoxide are seen (i.e., an amount of carbon monoxide of at least about 0.01 ppm in the patient's breath), then the attending physician or caregiver may then begin to administer therapeutic doses of carbon monoxide to treat oxidative stress or any one or more of the conditions or disease states which are secondary to or result in oxidative stress.

The following conditions or disease states may be treated using low dosages of CO in effective amounts pursuant to the teachings of the present invention. These include: asthma, emphysema, bronchitis, adult respiratory distress syndrome, sepsis, cystic fibrosis, pneumonia, interstitial lung diseases, idiopathic pulmonary diseases, other lung diseases including primary pulmonary hypertension, secondary pulmonary hypertension, cancers, including lung, larynx and throat cancer, arthritis, wound healing, Parkinson's disease, Alzheimer's disease, peripheral vascular disease and pulmonary vascular thrombotic diseases such as pulmonary embolism.

Low dosage CO may also be used in the present invention to induce HO-1 enzyme in patients and prevent or limit oxidative stress, especially oxidative stress caused by hyperoxia or sepsis. Induced HO-1 is implicated in maintaining homeostasis in the cells of the patient.

Low dosage CO may also be used to delay the onset of, or alleviate the effects of oxidative stress in transplant patients, in particular organ transplant patients, especially lung transplant patients. Low dosage CO may also be used to treat inflammatory conditions of the lungs or inflammation which occurs secondary to sepsis or rejection in transplant patients. While not being limited by way of theory, low dosage CO is believed to act as an anti-inflammatory agent by inhibiting the production and/or effect of pro-inflammatory cytokines such as TNF-α, IL-1, IL-6, MIP-1 and induces or promotes the action of anti-inflammatory cytokines IL-4 and IL-10.

The present invention also relates to the use of CO as a preservative for storing organs to be used in transplants. It is an unexpected result that the inclusion of low dosage CO in the storage media in which organs to be transplanted are stored will substantially reduce the likelihood of oxidative damage to the organs during storage and substantially enhances the storage time that organs to be transplanted may be safely stored without suffering irreversible oxidative damage. Thus, in this aspect of the present invention, an effective amount of CO is bubbled into storage media either before or preferably when an organ is first placed in the media or shortly thereafter. CO may also be used to enhance the storage stability of organs which have been stored for some time in media, but in those instances, oxidative damage may have become irreversible, thus limiting the intended effect.

Administration of compounds according to the present invention is generally through the mouth or nasal passages to the throat and lungs, where the CO may exert its effect directly or be readily absorbed into the patient's blood stream. The concentration of active compound (CO) in the therapeutic gaseous composition will depend on absorption, distribution, inactivation, and excretion (generally, through respiration) rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time. Acute, sub-acute and chronic administration of CO are contemplated by the present invention, depending upon the condition or disease state to be treated.

In delivering CO to patients or in other applications at concentrations ranging from about 0.001 to about 3,000 ppm pursuant to the present invention, gaseous compositions according to the present invention may be prepared by mixing commercially available compressed air containing CO (generally about 1% CO) with compressed air or gas containing a higher percentage of oxygen (including pure oxygen), and then mixing the gasses in a ratio which will produce a gas containing a desired amount of CO therein. Alternatively, compositions according to the present invention may be purchased pre-prepared from commercial gas companies. In a preferred embodiment, patients are exposed to oxygen ($O_2$ at varying doses) and CO at a flow rate of about 12 liters/minute in a 3.70 cubic foot glass exposure chamber. To make a gaseous composition containing a pre-determined amount of CO, CO at a concentration of 1% (10,000 ppm) in compressed air is mixed with >98% $O_2$ in a stainless steel mixing cylinder, concentrations delivered to the exposure chamber or tubing will be controlled. Because the flow rate is primarily determined by the flow rate of the $O_2$ gas, only the CO flow is changed to generate the different concentrations delivered to the exposure chamber or tubing. A carbon monoxide analyzer (available from Interscan Corporation, Chatsworth, Calif.) is used to measure CO levels continuously in the chamber or tubing. Gas samples are taken by the analyzer through a portion the top of the exposure chamber of tubing at a rate of 1 liter/minute and analyzed by electrochemical detection with a sensitivity of about 1 ppb to 600 ppm. CO levels in the chamber or tubing are recorded at hourly intervals and there are no changes in chamber CO concentration once the chamber or tubing has equilibrated. CO is then delivered to the patient for a time (including chronically) sufficient to treat the condition and exert the intended pharmacological or biological effect.

One of ordinary skill will readily recognize the symptoms of oxidative stress, inflammation, one or more of the conditions or disease states in which oxidative stress is implicated, sepsis or septic shock, and other conditions in which the delivery of CO represents a viable therapeutic option. All of these conditions or disease states are well known in the art.

In addition to using CO as a therapeutic agent, the measurement of CO may be a useful diagnostic tool to determine whether a patient is in oxidative stress or has a condition or a disease state where CO may be implicated. In this aspect of the present invention, a patient will have his or her exhaled breath analyzed for the presence of CO. CO content in a patient's breath is measured by a CO monitor (for example, using a Logan LR2000) which is sensitive to the detection of CO from 0 to about 1000 ppm (with a sensitivity as low as 1 ppb). In this method, the subjects exhale slowly from functional FVC into the breath analyzer with a constant flow (5-6 l/m) over a 20-30 second interval. Two successful recordings are made and mean values will be used for all calculations. Ambient CO levels are recorded before each breath in order to provide control or background values. While any elevation in CO levels from background numbers may implicate an actual or incipient state of oxidative stress, an amount of CO of at least about 1 ppm provides a clear indication that the patient is in or is about to suffer oxidative stress.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Evidence that CO Induces Tolerance to Lethal Hyperoxia and Oxidative Stress

In the following example, the effect of low dose administration of CO in hyperoxia in rats was assessed. In the examples presented, there is a demonstration that animals which were exposed to a low concentration of CO exhibit marked tolerance to otherwise lethal hyperoxia in vivo. The increased survival was associated with marked inhibition of hyperoxia-induced lung injury as assessed by pleural effusion and protein accumulation in the airways. Histological analysis of the lungs after hyperoxia demonstrates severe lung airway and parenchymal inflammation, fibrin deposition, and pulmonary edema. In contrast, the lungs of rats exposed to hyperoxia in the presence of CO were completely devoid of injury or inflammation. Neutrophil influx in to the airways of the lung, a reliable marker of oxidant-induced lung injury, and total lung apoptotic index were strikingly reduced in animals exposed to hyperoxia in the presence of CO. The modulation of neutrophil infiltration and apoptosis is postulated as a potential mechanism by which CO confers protection against oxidative stress in vivo.

Methods

Animals and Gas Exposure

Pathogen-free male Sprague-Dawley rats (250-300 g) were purchased from Harlan Sprague-Dawley (Indianapolis, Ind.) and allowed to acclimate upon arrival for 7 days prior to experimentation. Animals were fed rodent chow and water ad libitum. All experimental protocols were approved by the Animal Care and Use Committee.

Animals were exposed to >98% $O_2$ or 98% $O_2$+CO mixtures at a flow rate of 12 liters/min in a 3.70-cubic-foot glass exposure chamber. Animals were supplied food and water during the exposures. CO at a concentration of 1% (10,000 ppm) in compressed air was mixed with >98% $O_2$ in a stainless steel mixing cylinder prior to entering the exposure chamber. By varying the flow rates of CO into the mixing cylinder, concentrations delivered to the exposure chamber were controlled. Because the flow rate was primarily determined by the $O_2$ flow, only the CO flow was changed to generate the different concentrations delivered to the exposure chamber. A carbon monoxide analyzer (Interscan Corporation, Chatsworth, Calif.) was used to measure CO levels continuously in the chamber. Gas samples were taken by the analyzer through a port in the top of the exposure chamber at a rate of 1 liter/min and analyzed by electrochemical detection with a sensitivity of 10 ppm to 600 ppm. CO levels in the chamber were recorded at hourly intervals and there were no changes in chamber CO concentrations once the chamber had equilibrated. $O_2$ concentrations in the chamber were determined using a gas spectrometer.

Lung Tissue Preparation

Lungs were fixed by perfusion with 10% formalin at 20 cm $H_2O$ pressure and embedded in paraffin. Lung sections of 4-5 M were mounted onto slides pretreated with 3-aminopropylethoxysilane (Digene Diagnostics, Inc., Beltsville, Md.). Slides were baked for 30 min at 60° C. and washed twice in fresh xylene for 5 min to remove the paraffin. The slides were then rehydrated though a series of graded alcohols and then washed in distilled water for 3 min prior to staining with hematoxylin and eosin.

Bronchoalveolar Lavage (BAL) Analysis

Animals were anesthesized with sodium pentobarbital 24 h after LPS administration or 56 h of hyperoxia exposure. BAL (35 ml/kg) was performed 4 times with PBS (pH 7.4). Cells were pooled from the lavages and centrifuged at 1200 g for 10 min. The supernatant was discarded and cells were resuspended in PBS. Cell counts were performed using a Neubaur hemocytometer. For differential analysis, samples were cytocentrifuged and stained with Diff-Quik.

Measurement of Injury Markers

Rats were removed at 56 h of hyperoxia and anesthetized with sodium pentobarbital. The pleural effusion was collected by inserting an 18 gauge needle and 10 cc syringe through the diaphragm and withdrawing all fluid present in the pleural cavity. BAL was performed as described above, and the first lavage was centrifuged at 1200 g for 10 min and the supernatant was assayed for the protein albumin as determined by Bromcresol Green Kit (BCG) from Sigma (St. Louis, Mo.).

Arterial Blood Oxygen Tension and Carboxyhemoglobin Determination

Indwelling catheters were surgically implanted into the carotid arteries of rats anesthetized with 3% v/v isoflurane. Animals were secured in jackets and tethers to allow movement about the cage and access to food and water which were placed inside the exposure chambers. Polyethelene tubing, connected to the catheter and threaded out through an airtight fitting in the lid of the chamber, was used for continuous heparin infusion throughout the exposure (20 U/ml at 0.1 ml/h) to maintain patency of the vessel. At each time point, 1 cc of blood was drawn into a heparinized syringe, sealed and placed on ice until analyzed for oxygen tension. Arterial oxygen tension and carboxyhemoglobin were determined using a BG3 Instrumentation Laboratory Blood Gas Analyzer and Co-oximeter (Boston, Mass.).

Apoptosis by TUNEL Assay and Photomicrography

The TUNEL (terminal transferase dUTP nick end-labeling) method was used for apoptosis assay of lung tissue sections as previously described (Otterbein, et al., 1998, *Am. J. Physiol.* 275: L14-L20; and Kazzaz, et al., 1996, *J. Biol. Chem.* 271: 15182-15186.). TUNEL reagents including rhodamine-conjugated anti-digoxigenin Fab fragment were obtained from Boehringer Mannheim (Indianapolis, Ind.). Tissue sections were counterstained with 2 g/ml 4', 6-diamidine-2-phenylindole-dihydrocholride (DAPI) (Boehringer Mannheim) for 10 min at room temperature. Photomicro graphs were recorded on 35 mm film using a Nikon Optiphot microscope and UFX camera system (Nikon Inc., Melville, N.Y.) and transferred onto a KodakPhotoCD. The images were digitally adjusted for contrast using Adobe Photoshop 3.0 (Adobe Systems Inc., Mountain View, Calif.).

Computer Aided Image Analysis

To quantify the extent of apoptosis in the rat lung, samples were studied by epifluorescence to visualize either TUNEL-positive nuclei (590 nm) or total DAPI stained nuclei (420 nm). Images were captured with a CCD video camera. The captured images were analyzed using the Image 1 system (Universal Imaging, West Chester, Pa.). Images were digitally thresholded using identical settings for each set of either DAPI- or TUNEL-fluorescent groups. The total number of cells (nuclei) or the number of TUNEL-positive cells in each field was determined in the object counting mode. At least 100 fields were analyzed from at least three individual animals for each experimental group. The apoptotic index was calculated as the percent of TUNEL-positive apoptotic nuclei divided by the DAPI-staining nuclei.

Statistical Analysis

Data are expressed as the mean±SEM. Differences in measured variables between experimental and control groups were assessed using Student's t tests. Statistical calculations were performed on a Macintosh personal computer using the Statview II Statistical Package (Abacus Concepts, Berkeley, Calif.). Statistical difference was accepted at P<0.05.

Results

CO Induces Tolerance to Lethal Hyperoxia

We used clinically relevant in vivo models of oxidative stress to test the hypothesis that CO mediates the protective effects of HO-1 against oxidative stress. Hyperoxia when administered to animals produces pathophysiologic changes similar to those seen in human adult respiratory distress syndrome (ARDS) (Lee, et al., *Am. J. Resp Cell Mol Biol.* 14: 556-568; and Clerch, and Massaro, *J. Clin. Invest.* 91: 499-1508). We and others have shown that adult rats exposed to hyperoxia develop lung edema or pleural effusion by 56 h which significantly increases between 56 and 66 h (Lee, et al, supra, Clerch, supra and Choi, et al., *Am. J. Respir. Cell Mol. Biol.* 13: 74-82). These rats will uniformly die by 72 h of continuous hyperoxic exposure (Lee, et al. and Clerch, supra). In this study, one group of rats were placed in hyperoxia (>98% oxygen $O_2$) alone while the second group of rats were placed in an identical chamber and exposed to the same levels of hyperoxia in the presence of a low concentration of CO (250 ppm). Rats exposed to hyperoxia alone all died by 72 h (FIG. 1a) while rats exposed to hyperoxia in the presence of a low concentration of CO exhibited highly significant tolerance to hyperoxia: all animals were alive at the 72 h time point (FIG. 1). Table 1 demonstrates that this protective effect of CO is concentration dependent, with effects seen in the range between 50 ppm to 500 ppm. We observed concentration dependent protection against hyperoxia at both 72 and 100 h of hyperoxia exposure (Table 1). (P-value for the association between survival and CO concentration is 0.001 by logistic regression). Carboxyhemoglobin levels, a standard measurement of CO levels in the blood, correlated with increasing concentrations of CO exposure and survival of animals to lethal hyperoxia (Table 1, below). Rats exposed to low concentrations of CO (50-500 ppm) alone did not exhibit any untoward effects.

TABLE 1

Concentration-Depenent Protective Effects of CO Against Lethal Hyperoxia

| CO Concentration | % Survival | | % COHb | P Value |
|---|---|---|---|---|
| | 72 h | 100 h | | |
| 0 | 0 | 0 | 6.6 ± 0.4 | |
| 50 | 33 | 0 | 7.7 ± 0.4 | 0.004 |
| 100 | 50 | 50 | 9.3 ± 0.1 | 0.007 |
| 250 | 100 | 80 | 11.3 ± 0.06 | 0.004 |
| 500 | 100 | 80 | ND | |

Values are means±SE; n=12-15 rats in survival experiments and 3-4 rats for carboxyhemoglobin (HbCO) measurements. CO, carbon monoxide in parts per million. ND-not determined. Rats were exposed to hyperoxia (>98%) in the presence of CO at the indicated concentrations, and percent survival of rats and carboxyhemoglobin (%(HbCO) were determined. P values represent comparison of % HbCO levels with those in control rate (0 ppm). Significant differences in % HbCO between each CO concentration were observed (p<0.007).

CO Provides Protection Against Hyperoxia-Induced Lung Injury

Figure 1B:
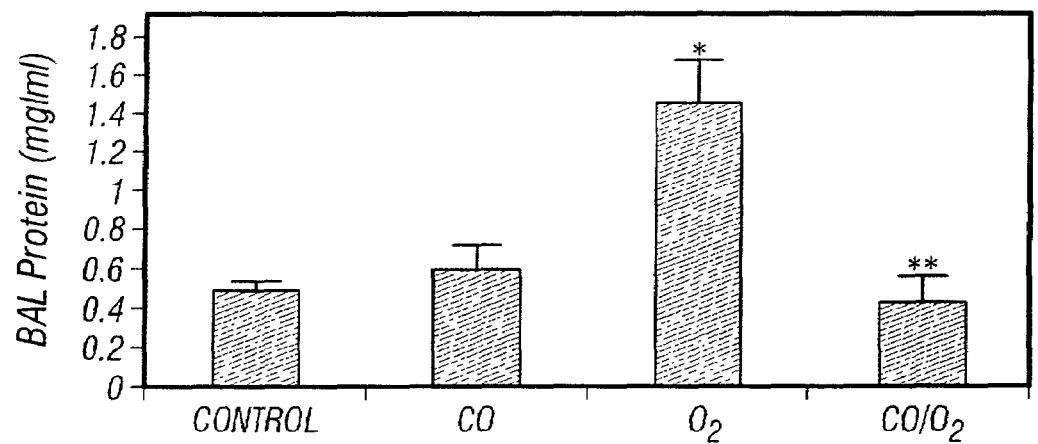

To assess further the beneficial effects of CO, we measured the volume of pleural effusion and total protein accumulation in the airways, both standard and highly reliable markers of hyperoxic lung injury (Lee, et al., Clerch and Choi, et al., supra). Rats exposed to hyperoxia alone exhibited an increase in the volume of pleural effusion after 56 h of hyperoxia exposure (FIG. 1a) while in those rats exposed to hyperoxia in the presence of a low concentration of CO, we observed a marked inhibition in the amount of pleural effusion (P<0.0001) (FIG. 1a). Rats exposed to hyperoxia alone exhibited a significant increase in the amount of protein accumulation into the airways as measured by bronchoalveolar lavage (FIG. 1b). In contrast, animals exposed to hyperoxia in the presence of CO exhibited significantly lower levels of protein accumulation (P<0.01) (FIG. 1b). The amount of pleural effusion or protein accumulation in the BAL in rats exposed to CO alone were similar to levels observed in control animals exposed to normoxia.

Effect of CO on Lung Histology

Figure 3:
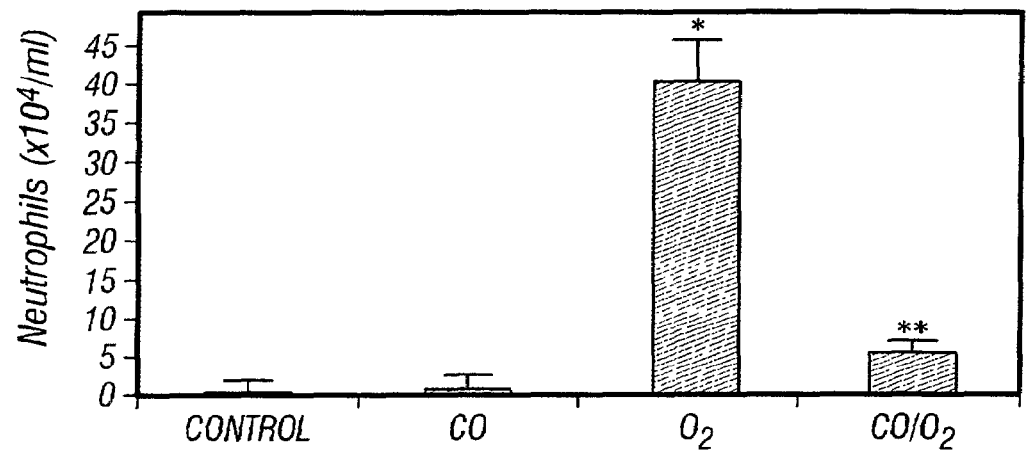
FIG. 3 shows the effect of CO administration on BAL cell count. Differential cell counts for neutrophils were performed on BAL fluid 56 hours after hyperoxia in the present and absence of CO (250 ppm). Data are means established for 6 rats.
Figure 4:
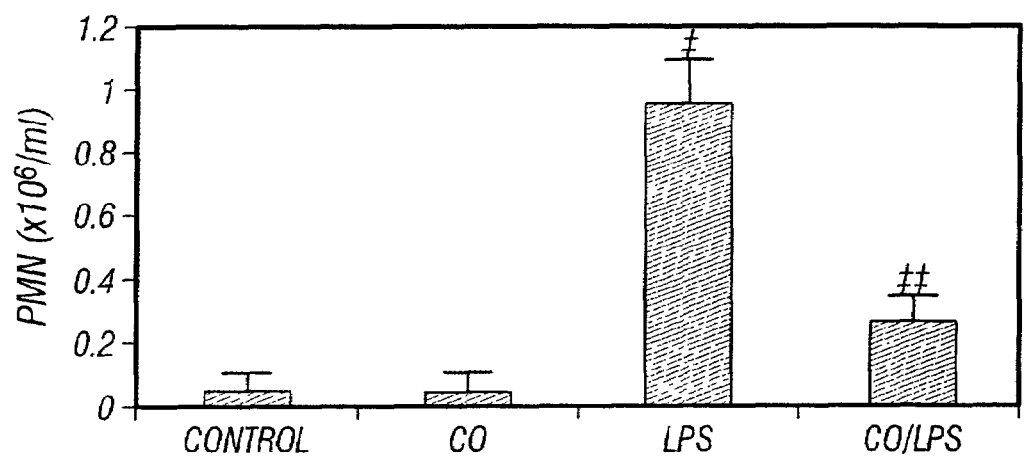
FIG. 4 shows the effect of CO administration on LPS-induced neutrophils into the lungs of rats.

We performed histological analyses to examine further whether a low concentration of CO attenuated lung injury. There were striking differences in lung histology between the two experimental groups as compared to control (FIGS. 2a and b). Marked lung hemorrhage, edema, alveolar septal thickening, influx of inflammatory cells, and fibrin deposition were observed in rats exposed to hyperoxia alone (FIG. 2c, and d). In contrast, the lungs of rats exposed to hyperoxia in the presence of CO were completely normal macroscopically and microscopically (FIG. 2, e and f). CO attenuates hyperoxia-induced neutrophil infiltration into the airways and total lung apoptotic index In order to further investigate possible mechanism(s) of CO-mediated protection against hyperoxia, we examined the inflammatory cell profile in the bronchoalveolar lavage of animals exposed to hyperoxia. The following findings provide a mechanism to explain the effects of low levels of CO. We hypothesized that CO may mediate the protection against oxidant tissue injury via inhibition of neutrophil influx into the airways. Animals exposed to hyperoxia alone demonstrated an increase in neutrophil influx into the airways as assessed by bronchoalveolar lavage analysis (FIG. 3) (P<0.007). In contrast, rats exposed to hyperoxia in the presence of CO exhibited significant reductions in neutrophil influx (P<0.006) (FIG. 3). Moreover, identical experiments were performed using a second model of oxidant-induced lung injury and inflammation. Lipopolysaccharide (3 mg/kg i.v.) administered to rats induces profound neutrophil influx into the airways as shown in FIG. 4. However, this neutrophil influx was significantly inhibited in the lungs of rats given LPS and exposed to CO (FIG. 4) (P<0.007).

Figure 5:
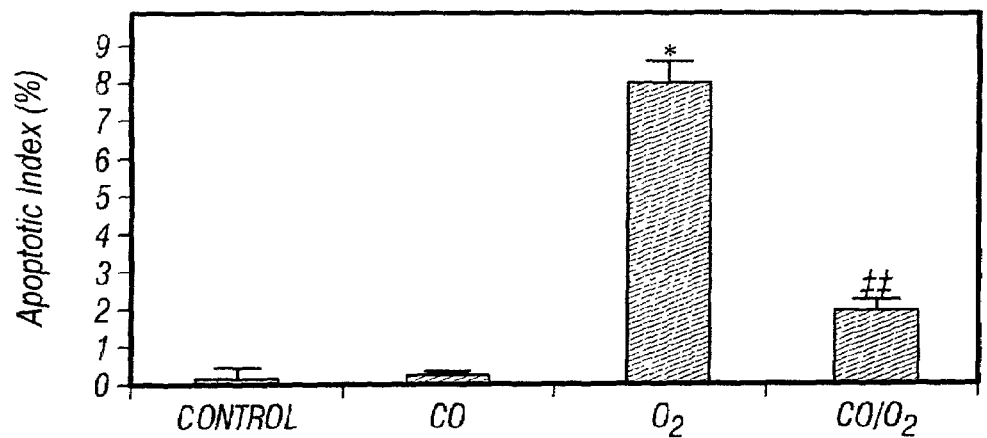
FIG. 5 shows the effect of CO administration on lung apoptotic index. After pretreatment with CO (250 ppm), lung tissues sections from rats were analyzed for terminal doxytransferase dUTP nick and labeling (TUNEL)-positive cells and costained to determine apoptotic index (number of TUNEL-positive cells/number of DAPI stained cells) after 56 hours hyperoxic exposure. DATA are means of samples from 3 rats.

Another possible mechanism by which CO might exert its salutary effects would be by inhibiting apoptosis. We have observed that rats exposed to hyperoxia alone exhibit a highly signifcant induction in the lung apoptotic index (7.9%±0.3), when compared to control rats in normoxia (0.5%±0.09) (P<0.0001) (FIG. 5). In contrast, rats exposed to hyperoxia in the presence of CO demonstrate a significant reduction in the lung apoptotic index (1.8%±0.12) when compared to animals exposed to hyperoxia alone (7.9%±0.3) (P<0.001) (FIG. 5).

Discussion

We have shown that exogenous administration of low concentrations of CO can provide protection against oxidative stress in models of inflammation. It should be noted that the concentration of CO used for these studies, in the order of 50-500 ppm, corresponds to 0.005% to 0.05% CO, respectively. A concentration of 500 ppm represents one twentieth of the lethal concentration of CO in our model (data not shown). It is notable that the concentrations of CO used for these studies were even lower (10-50 fold lower) than the doses administered to human beings (0.3% CO) to assess the diffusion capacity ($D_LCO$) of the lung, a standard pulmonary function test. Since differences in arterial $pO_2$ levels have been implicated in other models of tolerance to hyperoxia (Choi, et al., *Am. J. Respir. Cell Mol. Biol.* 13: 74-82), we measured the $PO_2$ content of our experimental groups. No significant difference was observed between rats exposed to hyperoxia and rats exposed to hyperoxia in the presence of a low concentration of CO (hyperoxia, $PO_2$ 502.5±7.4 mm Hg versus hyperoxia and CO, 510.5±11.4 mm Hg, P value NS).

The precise mechanism(s) by which CO mediates protection is not clear. Our observation that CO attenuated the influx of neutrophils into the airways is interesting in that it is well established that neutrophil influx in the bronchoalveolar lavage is of paramount importance in the development of hyperoxia-induced lung injury in in vivo models and in human patients with ARDS. The findings of our study provide a new mechanism to explain the anti-inflammatory properties of HO-1. Furthermore, the inhibition of apoptosis by CO may represent an additional mechanism by which CO provides protection against oxidant-induced injury and inflammation. Although the precise physiological function of apoptosis in the lung has yet to be established, emerging data strongly suggest that the total lung apoptotic index can serve as a useful marker of lung injury in response to oxidative stress such as hyperoxia. Soares et al also showed that HO-1 may act as an anti-apoptotic molecule in an in vitro model (29). We have also shown in vitro that HO-1 can inhibit TNF-α induced apotposis in L929 cells (unpublished observations). It seems possible, if not likely, that CO may be mediating the effects of HO-1 observed in those studies.

We have provided a mechanism in this paper to explain the protective functions attributed to HO-1 in models of lung injury. Carbon monoxide, a product of heme catabolism by HO, has similar protective effects in ameliorating the lung injury as does expression of HO-1. The concentrations of CO needed to achieve this dramatic therapeutic effect are far less than the known toxic concentrations, and even lower than the concentrations used in pulmonary function tests in humans. Our work evidences the expected therapeutic use of low concentrations of CO in clinical settings not only in lung disorders such as ARDS and sepsis but also in a variety of other inflammatory disease states.

Example 2

Studies on the Anti-Inflammatory Effects of Carbon Monoxide involving the Mitogen Activated Protein Kinase Pathway These studies were performed and are presented to describe the anti-inflammatory effects which carbon monoxide (CO), a by-product of heme catabolism mediates at low concentration pursuant to the present invention. In particular, low concentrations of CO differentially and selectively inhibits the expression of LPS-induced pro-inflammatory cytokines TNF-α, IL-1β, and MIP-1β and augments the LPS-induced expression of the anti-inflammatory cytokine IL-10. As a consequence of these studies, it is believed that CO plays an important protective role in inflammatory disease states with therapeutic implications for the treatment of sepsis, septic shock and related conditions.

Using this well established model of LPS-induced inflammation, we tested the hypothesis that CO, one of three major end products following the catabolism of heme by HO, exerts potent anti-inflammatory effects, and may mediate much or all of the anti-inflammatory effects observed with HO-1. We demonstrate for the first time that CO acts as a potent anti-inflammatory molecule both in vitro and in vivo. CO selectively inhibits the expression of the pro-inflammatory cytokines TNF-α, IL-1β, and MIP-1 β and augments production of the anti-inflammatory cytokine IL-10. Interestingly, we also demonstrate that CO mediates these anti-inflammatory effects independently of nitric oxide [See, Thomassen, et al., *Am. J. Respir. Cell Mol. Biol.* 17: 279-283 (1997)], or via cGMP, which is generally believed to mediate the effects of CO in other well established vascular and neuronal cell culture systems. See, Morita, et al. *Proc. Natl. Acad. Sci. USA.* 92, 1475-1479 (1995) and Verma, et al., *Science.* 259, 381-384 (1993). Rather, the data evidences that CO mediates these anti-inflammatory effects specifically via the mitogen activated protein kinase pathway, in particular the MKK3/p38 pathway.

Methods

Animals. Male C57BL/6 and IL-10 (−/−) mice were purchased from Jackson Laboratory (Bar Harbor, Me.), and allowed to acclimate for one week with rodent chow and water ad libitum. The MKK (−/−) mice were generated as previously described [Lu, et al., *EMBO J.* 18:1845-1857 (1999)]. Wild type littermates were used as controls. All animals were housed in accordance with guidelines from the American Association for Laboratory Animal Care and Research Protocols and were approved by the Animal Care and Use Committee of Yale University School of Medicine.

Reagents. All reagents were purchased from Sigma Chemical Co. (St Louis, Mo.) unless specified otherwise.

Plasmid Construct. Plasmid pSFFV/HO-1 was constructed by insertion of the rat HO-1 cDNA [Shibahara, et al., *Proc. Natl. Acad. Sci. USA.* 82: 7865-7869 (1985)] downstream of the Friend spleen focus-forming virus 5' long-terminal repeat in the mammalian expression vector pSFFV/neo [Fuhlbrigge, et al, *Proc. Natl. Acad. Sci. USA.* 85: 5649-5653 (1988)] (kindly provided by Stanley Korsmeyer).

Transfection. Stable transfections were carried out by the calcium phosphate precipitation technique as previously described [Alam, J., *J. Biol. Chem.* 269: 25049-25056 (1994)]. Briefly, RAW cells were plated ($1 \times 10^6$/10 cm plate) and 16 h later, transfected with 15 mg of pSFFV/neo or pSFFV/HO-1. Cells were exposed to the DNA-$CaPO_4$ precipitate for 6 h, shocked by a 1 min treatment with glycerol in phosphate-buffered saline and cultured for an additional 24 h in complete medium before addition of G418. Transfectants were selected over a 3-week period in the presence of G418 (up to 800 mg/ml) and individual clones were isolated by limited dilution.

Cell Culture Experimentation. RAW 264.7 mouse peritoneal macrophages were purchased from American Tissue Cell Culture (Rockville, Md.) and primary culture of rat pulmonary vascular smooth muscle cells were harvested from male Sprague Dawley rats (250-300 g) as previously described [Gunther, et al., *J. Cell. Biol.* 92: 289-298 (1982).]. Both cell types were grown in DMEM containing 10% FBS and gentamicin (100 mg/ml) in a humidified atmosphere of 5% $CO_2$/balanced air or 250 ppm CO/5% $CO_2$/balanced air. After a 2 h pretreatment with either CO or air, LPS (1 mg/ml) or sterile saline was added to the culture media and the culture plates were returned to the chamber(s). At various time points, cell plates were removed from the chamber to collect media and/or cells for Western analysis.

CO Exposures. Mice or macrophages were exposed to compressed air or 250 ppm CO. For cell culture experiments, 5% $CO_2$ was also present for buffering requirements. CO at a concentration of 1% (10,000 ppm) in compressed air was mixed with compressed air with or without $CO_2$ in a stainless steel mixing cylinder before delivery into the exposure chamber. Flow into the 3.70-$ft^2$ plexiglass animal chamber was maintained at 12 L/min and into the 1.2 $ft^2$ cell culture chamber at a flow of 2 L/min. The cell culture chamber was humidified and maintained at 37° C. A CO analyzer (Interscan, Chatsworth, Calif.) was used to measure CO levels continuously in the chambers. Gas samples were taken by the analyzer through a port in the top of the chambers at a rate of 1 L/min and analyzed by electrochemical detection, with a sensitivity of 10-600 ppm. Concentration levels were measured hourly and there were no fluctuations in the CO concentrations once the chamber had equilibrated (approximately 5 min).

Animal Experimentation. Mice were prebled from the retroorbital sinus (0.25 ml) and then exposed to CO (250 ppm) or room air for 1 h prior to administration of LPS (1 mg/kg, i.p.), *E. coli* serotype O127:B8. 1 and 16 h thereafter, they were removed from the exposure apparatus individually and a blood sample was obtained via the retroorbital sinus. After the blood collection, the mice were immediately returned to the exposure chamber. For hypoxia studies, mice were pretreated 1 h with 10% oxygen (hypoxia) and then administered LPS (1 mg/kg, i.p.). One h thereafter, they were removed from the exposure chamber individually and a blood sample was collected from the retroorbital sinus and the serum analyzed for TNF-a by ELISA. The $O_2$ concentration in the chamber was verified by an $O_2$ sensor calibrated for low $O_2$ tensions. (VWR, Boston, Mass.).

Cytokine Analysis. Serum and media samples were analyzed by ELISA kits purchased from R&D (Minneapolis, Minn.) following manufacturer's instructions.

Western Blotting. Assay kits were purchased from New England Biolabs (Beverly, Mass.) and used per manufacturer's instructions. The protocol is described briefly: at set time points, cells were removed from the exposure chamber, rinsed with cold PBS and then 200 ml of SDS sample buffer (62.5 mM Tris-HCl (pH 6.8), 2% w/v SDS, 10% glycerol, 50 mM DTT and 0.1% w/v bromphenol blue) was added to each plate. Cells were scraped and sonicated for 5 seconds. 20 ml of each sample was boiled for 5 min and then loaded into a 12% polyacrylamide gel and electrophoresed at 125 V for 90 min. The gel was transferred overnight at 40 volts onto nitrocellulose membrane. Membranes were then incubated with blocking buffer (5% nonfat dry milk in TTBS (10% tween in tris buffered saline) for 3 h), washed with TTBS and then incubated overnight in the corresponding rabbit polyclonal primary antibody directed against either phosphorylated ERK, p38, or JNK. HO-1 and TNF-a blots were probed for 1 h in blocking buffer with either rabbit anti-HO-1 or rabbit anti-TNF-a respectively (HO-1; Stressgen, Victoria Canada. TNF-α; Santa Cruz Biotechnology Inc., Santa Cruz, Calif.). After incubation in primary antibody, the membranes were washed in TTBS and proteins were visualized using horseradish peroxidase conjugated anti-rabbit IgG and the enhanced chemiluminesence assay, (Amersham Life Sciences, Arlington Heights, Ill.) according to manufacturer's instructions All MAPK membranes were subsequently stripped using standard stripping solution (100 mM beta-mercaptoethanol, 2% SDS and 62.5 MM Tris-HCl pH 6.8) at 50° C. and then reprobed with rabbit polyclonal antibody targeting total non-phosphorylated ERK, p38 or JNK to assure equal loading of protein.

RNA Extraction and Northern Blot Analysis

Total RNA was isolated by the STAT-60 RNAzol method with homogenization of the lung tissues in RNAzol lysis buffer followed by chloroform extraction (Tel-Test "B" Inc., Friendswood, Tex.). Northern blot analyses were performed as previously described (Otterbein, et al., *J. Clin. Invest.* 103, 1047-1054 (1999)). Briefly, 10 mg of total RNA was electrophoresed in a 1% agarose gel and then transferred to Gene Screen Plus nylon membrane (Dupont, Boston, Mass.) by capillary action. The nylon membranes were then prehybridized in hybridization buffer (1% bovine serum albumin [BSA], 7% sodium dodecyl sulfate [SDS], 0.5 M phosphate buffer, pH 7.0, 1.0 mM ethylenediamine tetraacetic acid [EDTA] at 65° C. for 2 h followed by incubation with hybridization buffer containing 32 p labeled rat HO-1 cDNA at 65° C. for 24 h. The cDNA was labeled with $^{32}$P-CTP using the random primer kit from Boehringer Mannheim (Boehringer Mannheim, Germany). Nylon membranes were then washed twice in wash buffer A (0.5% BSA; 5% SDS, 40 nM phosphate buffer pH 7.0, 1 mM EDTA) for 15 min each at 65° C. followed by washes in buffer B (1% SDS, 40 mM phosphate buffer, pH 7.0, 1.0 mM EDTA) for 15 min three times each at 65° C. Ethidium bromide staining of the gel was used to confirm the integrity and equal loading of the RNA.

Nitrate/Nitrite Analysis. Both analytes were measured in the cell culture media which had been ultrafiltered to remove all proteins greater than 10,000 molecular weight. All samples were than analyzed according to the assay kit protocols. (R & D, Minneapolis, Minn.).

cGMP Radioimmunoassay (RIA) in macrophages. Macrophages or vascular smooth muscle cells were exposed to CO (250 ppm) or air. 20 min before the end of the exposure 1 mM of 3-isobutyl-1-methylxanthine (IBMX) was added to the cells to prevent phosphodiesterase degradation of cGMP. After 2 h of exposure, cells were removed from the exposure chamber, rinsed with PBS and then 0.5 ml of 75% EtOH was added to the plate and cells were scraped and disrupted via sonication for 5 s. Samples were then centrifuged at 2000 g for 10 min. Supernatants were transferred to fresh tubes and evaporated to dryness. cGMP concentration in the cell extracts was determined by radioimmunoassay (NEN, Boston, Mass.) according to manufacturer's instructions. cGMP was normalized to protein concentration as determined by Bradford assay.

Statistical Analysis. Data are expressed as the mean±SE. Differences in measured variables between experimental and control group were assessed using Student's t tests. Statistical calculations were performed on a Macintosh personal computer using the Statview II Statistical Package (Abacus Concepts, Berkeley, Calif.). Statistical difference was accepted at $P < 0.05$.

Results

Over-Expression of HO-1 Inhibits TNF-α Production in Macrophages

Figure 6:
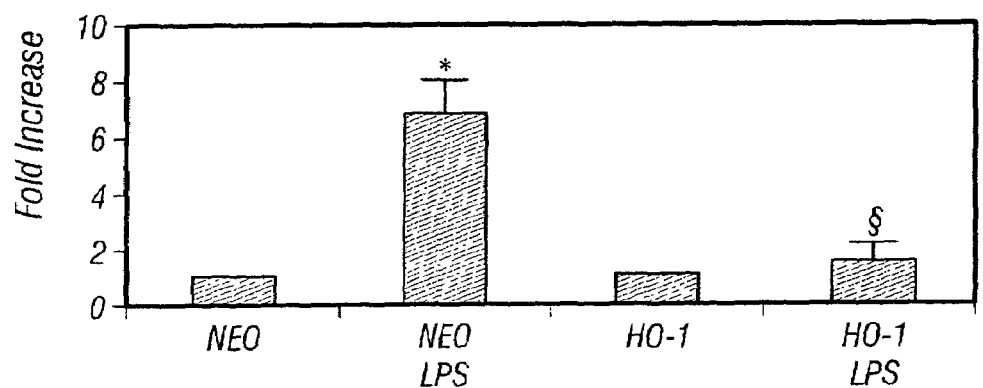
FIG. 6 shows the effects of overexpression of HO-1 in macrophages on LPS-induced TNF-α production.

Macrophage cell lines (RAW 264.7) over-expressing HO-1 were generated using an pSFFV-LTR promoter driven HO-1 expression plasmid. Nine clones were isolated and checked for HO-1 expression by Western blot analyses. We observed increased HO-1 expression in these clones (FIG. 1*a*; lanes c-k) when compared to the control, neomycin gene transfected cells (data not shown). We exposed cells to LPS (1 ng/ml) and measured the amount of TNF-production by ELISA. As expected, there was marked induction of TNF-a production in the control cells. In contrast, cells over-expressing HO-1 exhibited significantly attenuated amounts of TNF- after LPS treatment as compared to control cells (FIG. 6). We performed identical experiments in a second RAW 264.7 clone over-expressing HO-1 and observed similar results (data not shown).

Figure 7A:
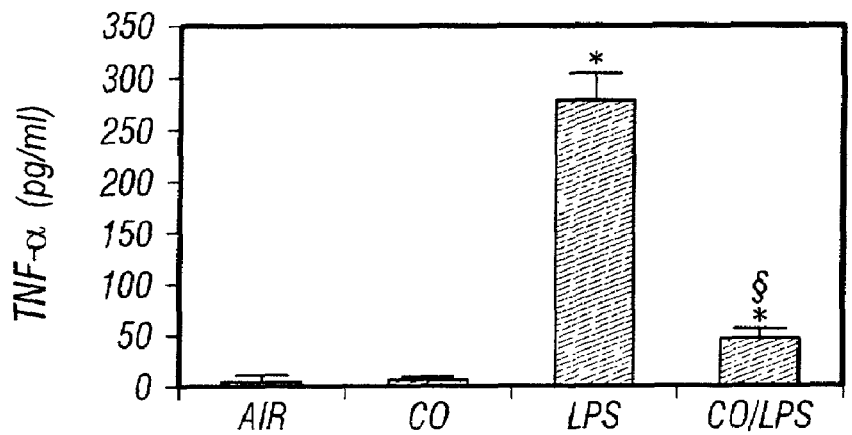
FIGS. 7A-7E show the results of experiments involving the effects of carbon monoxide on LPS-induced cytokine production in macrophages after pretreatment with CO (250 ppm).
Figure 7B:
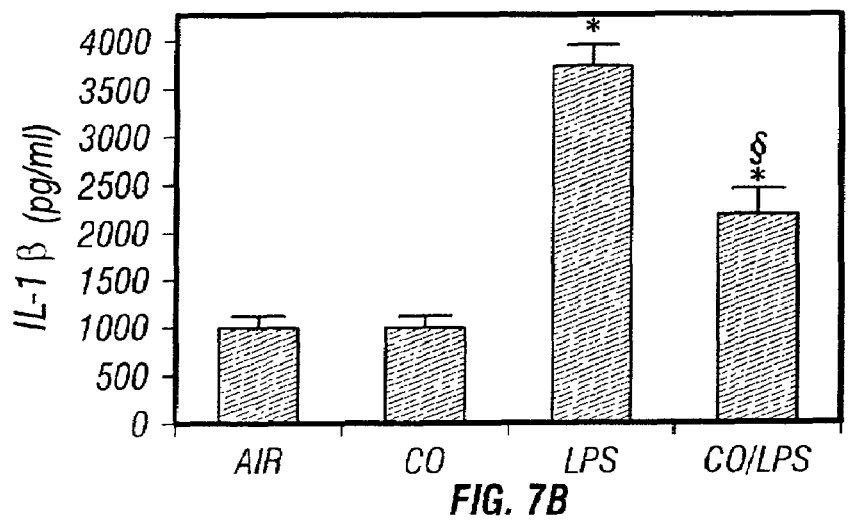
Figure 7C:
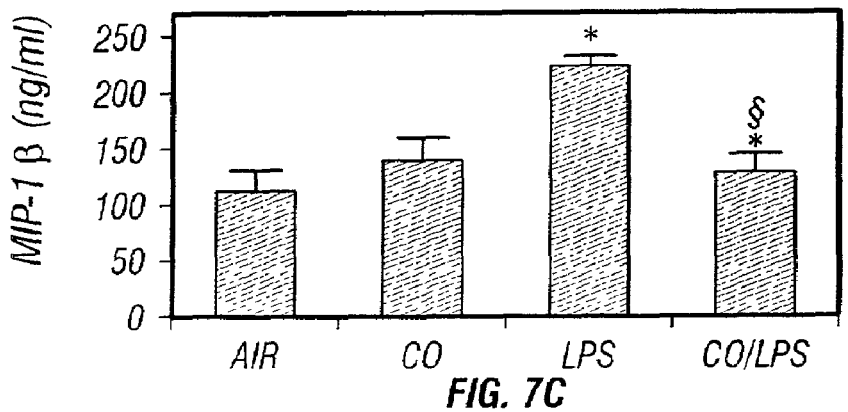
Figure 7D:
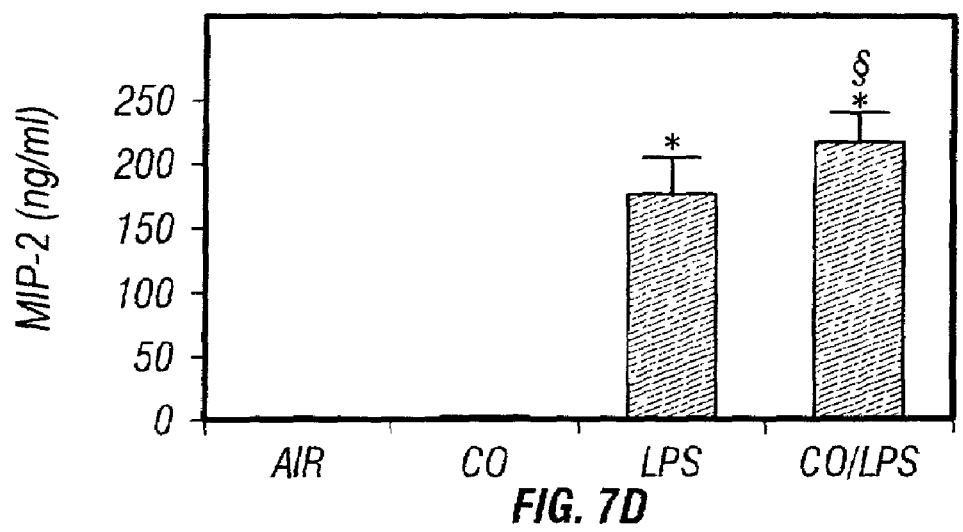
Figure 7E:
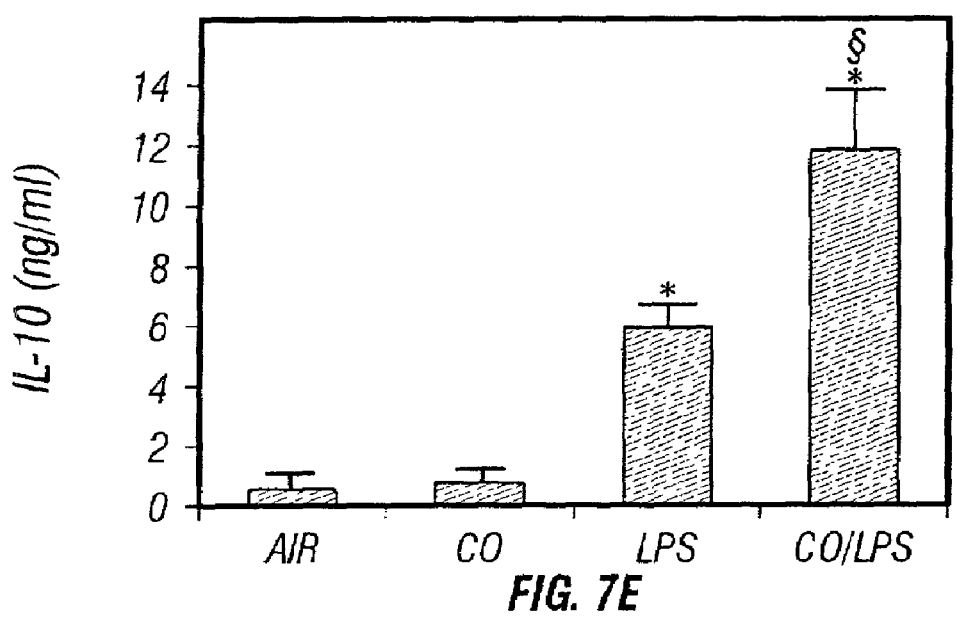

CO Selectively Targets Both Pro-Inflammatory and Anti-Inflammatory Cytokines in vitro After observing that HO-1 over-expressing macrophages exhibited reduced LPS-induced TNF-α production (FIG. 6), we tested the hypothesis that exposure of cells to a low concentration of CO, a major by-product released during the catalysis of heme by HO, could elicit similar responses in macrophages. We exposed wild type RAW 264.7 macrophages to LPS (1 mg/ml) in the presence or absence of CO (250 ppm) and TNF-production was measured by ELISA. As expected, cells exposed to LPS alone exhibited increased levels of TNF-α. However, cells exposed to LPS in the presence of CO exhibited significantly attenuated levels of TNF-α (FIG. 7*a*) which was concentration dependent (range of 10-500 ppm; data not shown). The attenuation by CO exerted similar inhibitory effects on the inflammatory cytokines IL-1β and MIP-1β (FIG. 7*b* and FIG. 7*c*) while not affecting the chemokines MIP-2 (FIG. 7*d*), JE, IFN-g or KC (data not shown). Importantly, in terms of the balance of pro- and anti-inflammatory cytokines, CO at 250 ppm significantly augmented the LPS-induced accumulation of the anti-inflammatory cytokine IL-10 (FIG. 7*e*).

Figure 8A:
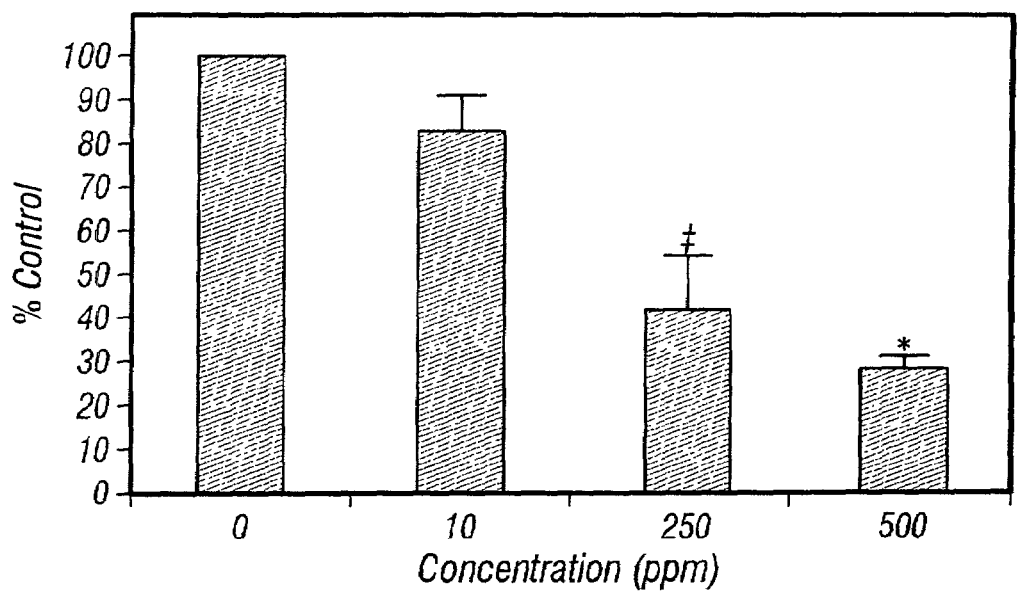
FIGS. 8A and 8B show the results of experiments which evidence that CO inhibits LPS-induced production of TNF-α and IL-10 after exposure to carbon monoxide. Six to eight mice in each treatment group.
Figure 8B:
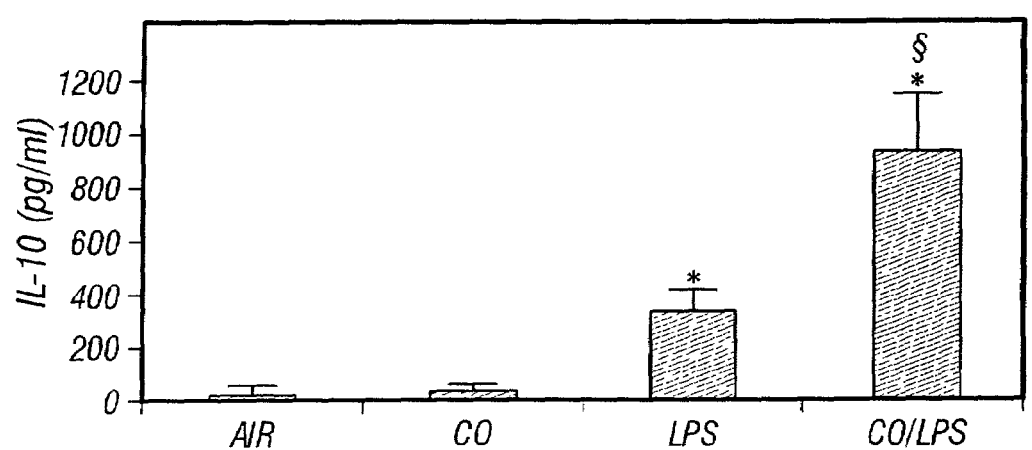

CO Selectively Targets Both Pro-Inflammatory and Anti-Inflammatory Cytokines In Vivo To examine whether the differential effects of CO on both pro-inflammatory and anti-inflammatory cytokines observed above in vitro also occurred in vivo, we administered a sub-lethal dose of LPS (1 mg/kg) to mice in the presence or absence of CO (using the same concentrations used in vitro). We observed that mice also exhibited a significant attenuation of TNF-α production in the presence of CO (FIG. 8*a*), and that CO attenuated LPS-induced TNF-α production in vivo in a dose-dependent manner (FIG. 8*b*) with an $EC_{50}$ of 69.9 ppm. Consistent with our own findings in vitro, we observed an augmentation of IL-10 in response to LPS in the presence of CO in vivo at a concentration of 250 ppm. To investigate whether hypoxia was involved in the inhibitory effects observed with CO on LPS-induced TNF-α production, we administered LPS (1 mg/kg) in a separate group of animals in the absence or presence of hypoxic (10% oxygen) conditions. Hypoxia had no effect on LPS-induced TNF-α production (data not shown).

CO Exerts Anti-Inflammatory Effects Via a cGMP Independent Pathway

To delineate the possible mechanism(s) by which CO exerts its effects, we examined whether the response to CO involved the guanylyl cyclase-cGMP pathway, which has been shown to mediate the biological effects of CO in vascular and neuronal cells [Morita, et al., *Proc. Natl. Acad. Sci. USA.* 92, 1475-1479 (1995) and Verma, et al., *Science.* 259, 381-384 (1993)]. Macrophages and vascular smooth muscle cells (used as a positive control) were exposed to 250 ppm CO. After 2 h of exposure, cell lysates were analyzed for cGMP by radioimmunoassay. Smooth muscle cells showed a 16 fold increase in cGMP content after CO exposure (#p<0.001) while the RAW 264.7 macrophages exhibited no significant increase in cGMP after exposure to CO (Table 2, below). To confirm the lack of a role of cGMP in CO treated macrophages, an analog of cGMP, 8-Br-cGMP, a compound that is non-degradable by phosphodiesterase yet maintains similar functional activity, was added to the macrophage culture followed by LPS to observe its effects on TNF-α production. As shown in Table 2, below, macrophages exposed to CO exhibited no increase in cGMP levels while the analog of cGMP, 8-Br-cGMP, had no effect on LPS-induced TNF-α production.

TABLE 2

Effects of CO on cGMP and LPS-Induced
TNF-α Production in RAW 264.7 Macrophages

| Treatment | cGMP (pmol/mg protein) | TNF-α (pg/ml) |
|---|---|---|
| Air | 4.25 ± 0.5 | 12 ± 10 |
| CO | 3.95 ± 0.6 | 15 ± 5 |
| LPS | ND | 660 ± 60$^a$ |
| CO/LPS | ND | 230 ± 40$^b$ |
| 8-Br-cGMP | ND | 18 ± 6 |
| 8-Br-cGMP/LPS | ND | 530 ± 35 |
| VSM/Air | 0.5 ± 0.4 | ND |
| VSM/CO | 8.1 ± 2$^c$ | ND |

$^a$p < 0.001 vs. CO, air, 8-Br-cGMP
$^b$p < 0.03 vs. LPS
$^c$p < 0.001 vs. air

CO Exerts Anti-Inflammatory Effects Via a Nitric Oxide Independent Pathway

Figure 9A:
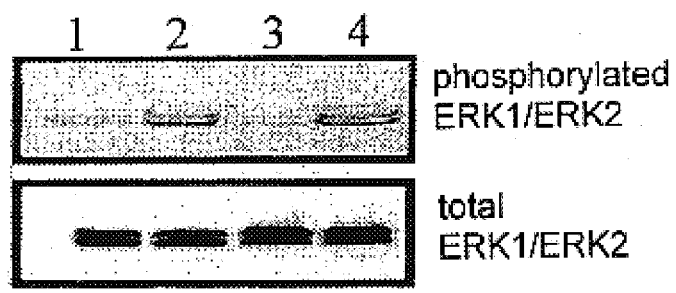
FIGS. 9A-9C show the effects of CO on LPS-induced activation of MAP kinases. In lane 1 is untreated control; lane 2, LPS; lane 3, CO alone; lane 4, LPS and CO.
Figure 9B:
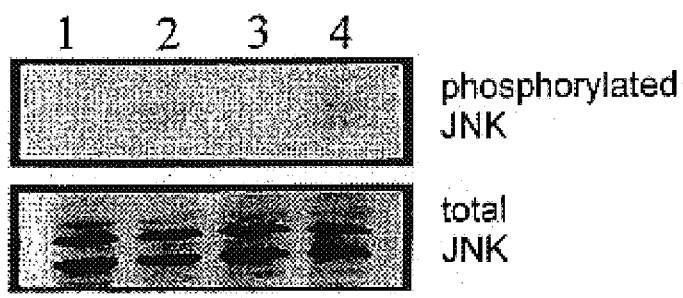
Figure 9C:
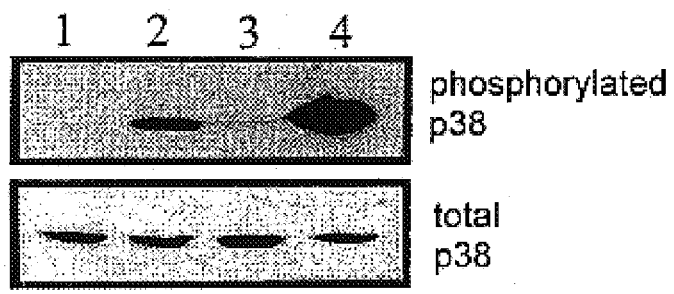

Based on our observation that CO exerts the anti-inflammatory effects via a cGMP independent pathway, and that CO can bind to the heme moiety of NOS, thereby modulating nitric oxide (NO) production [Tetreau, et al., *Biochemistry* 38: 7210-7218 (1999)], we investigated whether NO could indirectly mediate the anti-inflammatory effects observed with CO. We pretreated RAW 264.7 macrophage cells with L-NAME, an inhibitor of NOS, prior to exposing cells to LPS (1 mg/ml) in the presence of CO. As shown in FIG. 9, cells pretreated with L-NAME in the presence of CO and LPS exhibited similar levels of TNF-α compared to cells exposed to CO and LPS only. Further studies looking at LPS-induced NO production in RAW 264.7 cells found no increases in either nitrate or nitrite levels at 1 h post LPS in either the presence or absence of CO. Nitrite and nitrate levels did increase significantly, 50 fold respectively, but only after 16 h following LPS when compared to control cells, as has been shown previously [Nussler, et al., *J. Exp. Med.* 176: 261-264 (1992)]. This data further supported the notion that CO could not be acting indirectly via NO to modulate TNF-α production.

Differential Modulation of MAP Kinases by CO

Figure 11A:
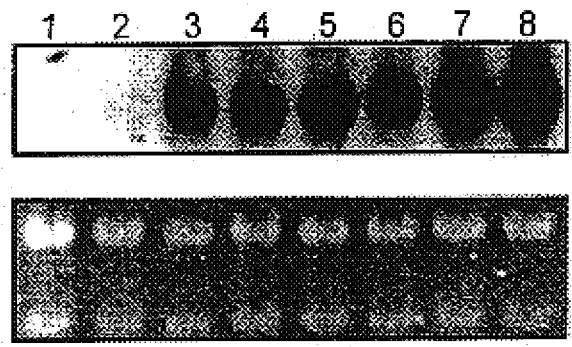
FIGS. 11A-11C show the effect of CO on LPS-induced TNF-α by measuring total RNA from RAW 264.7 cells after treatment with LPS in the absence or presence of CO and analyzing for TNF-α mRNA expression by northern blot analysis.

Based on our observations that CO acts via a cGMP or NO independent pathway, we sought a possible alternative mechanism by which CO might mediate anti-inflammatory actions. As previously described, administration of LPS to macrophages results in the activation of the MAPK pathway. See, Liu, et al., *J. Immunol.* 153, 2642-2652 (1994); Hambleton, et al., *Proc. Natl. Acad. Sci. USA.* 93, 2274-2778 (1996); Han, et al., *J. Biol. Chem.* 268, 25009-25014 (1993); Han, et al., *Science* 265, 808-811 (1994); Sanghera, et al., *J. Immunol.* 156, 4457-4465 (1996); and Raingeaud, J., et al., *J. Biol. Chem.*, 270, 7420-7426 (1995). Activation of the p38, ERK1/ERK2 and JNK pathways in macrophages by LPS was therefore first confirmed (FIGS. 11a, b and c; lane 2). In the presence of CO, LPS-induced ERK1/ERK2 and JNK MAP kinase activation was not affected, but p38 MAP kinase activation was significantly augmented. We also observed augmentation of MKK3/MKK6, kinases upstream to p38, by LPS in the presence of CO in RAW 264.7 cells when compared to cells treated with LPS alone (data not shown).

CO Mediates Anti-Inflammatory Effects Via the MKK3 MAP Kinase Pathway In Vivo.

Figure 10A:
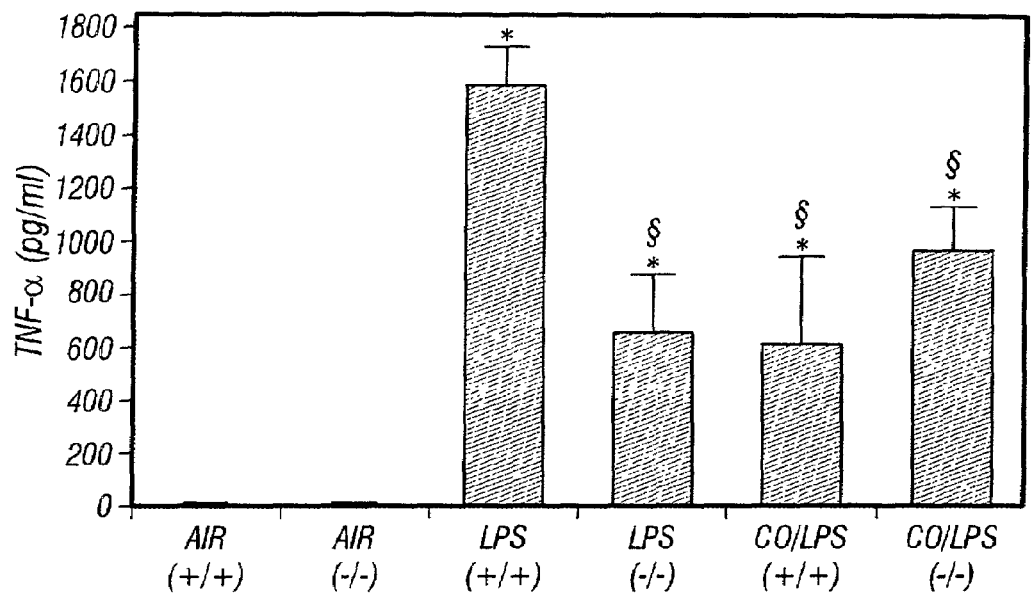
FIGS. 10A and 10B show the effects of CO on LPS-induced serum production of TNF-u and IL-b in Mkk3+ mice after exposure to CO. Six to eight mice were tested in each group.
Figure 10B:
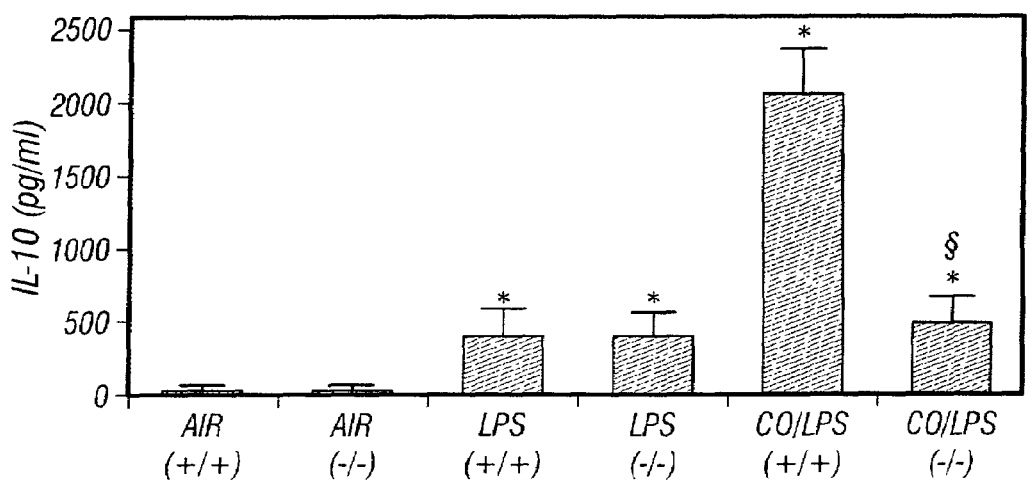

Since the p38 MAP kinase pathway was activated by LPS and augmented by CO we tested whether attenuation of this pathway led to a loss of the response. There are three MAP kinase kinases that activate the p38 MAP kinase, MKK3, MKK4 and MKK6 [Derijard, et al., *Science* 267, 682-685 (1995); and Raingeaud, et al., *Mol. Cell. Biol.* 16, 1247-1255 (1996)]. Since MKK3$^{(-/-)}$ macrophages would have deficient p38 activation in response to LPS and knowing that MKK3 plays a major role in the activation of p38, we hypothesized that administration of LPS to the MKK3$^{(-/-)}$ mice would substantiate the in vitro findings whereby CO augmented the LPS-induced p38 activation. Another rationale for using MKK3$^{(-/-)}$ mice was based on our in vitro observations that CO selectively augmented the LPS-induced p38 MAP kinase but affected neither the ERK1/ERK2 nor JNK pathways. A sublethal dose of LPS (1 mg/kg) was administered to MKK3$^{(-/-)}$ mice and wild type$^{(+/+)}$ littermates in the presence or absence of 250 ppm CO. As expected, wild type mice exhibited a marked increase in serum TNF-α production [Bauss, et al., *Infect. Immun.* 55, 1622-1625 (1987)] while the MKK3$^{(-/-)}$ mice exhibited decreased TNF-α serum levels when compared to LPS treated wild type$^{(+/+)}$ mice. This was expected since the MKK3/p38 MAPK pathway plays a major role, but certainly not exclusive one in mediating LPS-induced TNF-α: production. (FIG. 10a) See, Hambleton, et al., *J. Exp. Med.* 177, 1205-1208 (1993); Derijard, et al., *Science* 267, 682-685 (1995); Badger, et al., *J. of Pharm. & Exp. Therap.* 279, 1453-61 (1996); Wysk, et al., *Proc. Natl. Acad. Sci. USA.* 96, 3763-3768 (1999); and Geppert, et al., *Mol. Med.* 1, 93-103 (1994). Furthermore, wild type$^{(+/+)}$ mice demonstrated attenuated levels of LPS-induced TNF-α production in the presence of CO when compared to wild type$^{(+/+)}$ mice treated with LPS alone. This inhibitory effect of CO was lost in the MKK3$^{(-/-)}$ mice: CO did not affect LPS-induced TNF-α production in the MKK3$^{(-/-)}$ mice. In addition as shown in FIG. 10b, CO augmented LPS-induced IL-10 levels in the wild type$^{(+/+)}$ mice when compared to wild type$^{(+/+)}$ mice treated with LPS alone. However, the MKK3$^{(-/-)}$ mice did not exhibit augmented serum IL-10 levels after treatment with LPS in the presence of CO when compared to MKK3$^{(-/-)}$ treated with LPS alone. Exposure to either air or CO (250 ppm) had no effect on TNF-α or IL-10 production in either the MKK3$^{(-/-)}$ or wild type$^{(+/+)}$ mice.

It is well established that IL-10 is an inhibitor of pro-inflammatory cytokine synthesis and as such can limit the inflammatory process including TNF-α production. See, Howard, et al., *J. Exp. Med.* 177, 1205-1208 (1993). Therefore, we hypothesized that the augmentation of LPS-induced IL-10 production in the CO/LPS treated animals was responsible for the inhibition of TNF-α production. To test this hypothesis, we administered LPS to IL-10$^{(-/-)}$ null mice in the presence or absence of CO (250 ppm). Serum TNF-α levels measured at 1 h were inhibited in both the IL-10$^{(-/-)}$ as well as the wild type controls (66% and 73% inhibition, respectively) suggesting that the reduction in TNF-α levels observed in those animals exposed to CO/LPS was not due to augmented IL-10 production. In vitro studies using neutralizing antibodies to IL-10 in macrophages showed similar findings, in that CO-mediated TNF-α suppression occurred independently of IL-10 (data not shown).

CO Exerts Post-Transcriptional Regulation of LPS-Induced TNF-α Production

Figure 11B:
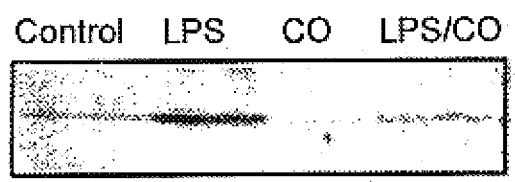
Figure 11C:
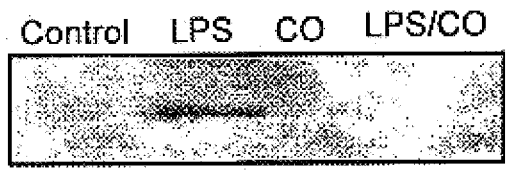

We attempted to delineate the mechanism by which CO augments the p38 pathway while down regulating TNF-α production. RAW 264.7 cells exhibit increased TNF-α mRNA after LPS treatment in the presence of CO, similar to levels observed in cells treated with LPS alone. Interestingly, cell lysates and media collected from these cells demonstrated decreased TNF-α protein expression by Western blot analyses after LPS in the presence of CO. We also observed decreased (>80% inhibition) TNF-α production in the media collected from these same cells by ELISA analysis, confirming our observations shown previously in FIG. 11b.

In sum, the experiments presented herein evidence that the administration of effective amounts of CO is a useful in vivo treatment for inflammation mediated through pro-inflammatory cytokines. Thus, the present invention may be used to treat inflammation which occurs secondary to sepsis or in conditions or disease states in which oxidative stress also occurs.

It is to be understood by those skilled in the art that the foregoing description and examples are illustrative of practicing the present invention, but are in no way limiting. Variations of the detail presented herein may be made without departing from the spirit and scope of the present invention as defined by the following claims.

The invention claimed is:

1. A method of treating emphysema secondary to or resulting in oxidative stress to a patient, comprising:
identifying a patient suffering from emphysema secondary to or resulting in oxidative stress; and
administering to the patient a therapeutically effective amount of a gaseous composition comprising carbon monoxide at a concentration of about 10 ppm to about 3000 ppm, wherein the patient inhales the gaseous composition.

2. A method of treating bronchitis secondary to or resulting in oxidative stress to a patient, comprising:
identifying a patient suffering from bronchitis secondary to or resulting in oxidative stress; and
administering to the patient a therapeutically effective amount of a gaseous composition comprising carbon monoxide at a concentration of about 10 ppm to about 3000 ppm, wherein the patient inhales the gaseous composition.

3. A method of treating cystic fibrosis secondary to or resulting in oxidative stress to a patient, comprising:
identifying a patient suffering from cystic fibrosis secondary to or resulting in oxidative stress; and
administering to the patient a therapeutically effective amount of a gaseous composition comprising carbon monoxide at a concentration of about 10 ppm to about 3000 ppm, wherein the patient inhales the gaseous composition.

4. A method of treating pneumonia secondary to or resulting in oxidative stress to a patient, comprising:
identifying a patient suffering from pneumonia secondary to or resulting in oxidative stress; and
administering to the patient a therapeutically effective amount of a gaseous composition comprising carbon monoxide at a concentration of about 10 ppm to about 3000 ppm, wherein the patient inhales the gaseous composition.

5. A method of treating interstitial lung disease secondary to or resulting in oxidative stress to a patient, comprising:
identifying a patient suffering from interstitial lung disease secondary to or resulting in oxidative stress; and
administering to the patient a therapeutically effective amount of a gaseous composition comprising carbon monoxide at a concentration of about 10 ppm to about 3000 ppm, wherein the patient inhales the gaseous composition.

6. A method of treating adult respiratory distress syndrome secondary to or resulting in oxidative stress to a patient, comprising:
identifying a patient suffering from adult respiratory distress syndrome secondary to or resulting in oxidative stress; and
administering to the patient a therapeutically effective amount of a gaseous composition comprising carbon monoxide at a concentration of about 10 rpm to about 3000 ppm, wherein the patient inhales the gaseous composition.

7. The method of claim 1, wherein the gaseous composition is a mixture comprising carbon monoxide, nitrogen and oxygen.

8. The method of claim 7, wherein the concentration of carbon monoxide in the mixture is monitored with a carbon monoxide analyzer.

9. The method of claim 1, wherein the patient is a human.

10. A method of treating asthma in a human patient, comprising:
identifying a human patient suffering from asthma; and
administering to the patient a therapeutically effective amount of a gaseous composition comprising carbon monoxide at a concentration of about 10 ppm to about 3000 ppm, wherein the patient inhales the gaseous composition.

11. A method of treating asthma in a patient, comprising:
identifying a patient suffering from asthma; and
administering to the patient a therapeutically effective amount of a composition comprising carbon monoxide, wherein the composition contains 0.005% to 0.05% carbon monoxide, wherein the composition is administered as an inhaled gas.

12. The method of claim 11, wherein the patient is a human.

13. A method of treating inflammation in a patient, comprising:
identifying a patient suffering from inflammation of at least one organ selected from a group consisting of: kidney, heart, and lung; and
administering to the patient a therapeutically effective amount of a gaseous composition comprising carbon monoxide at a concentration of about 10 rpm to about 3000 ppm, wherein the inflammation is of a type selected from a group consisting of: acute, allergic, alternative, atrophic, catarrhal, croupous, fibrinopurulent, fibrinous, immune, hyperplastic, proliferative, subacute, serous and serofibrinous inflammation, and wherein the patient inhales the gaseous composition.

14. A method of treating inflammation in a human patient, comprising:
identifying a human patient suffering from inflammation of at least one organ selected from a group consisting of: kidney, heart, and lung; and
administering to the patient a therapeutically effective amount of a gaseous composition comprising carbon monoxide at a concentration of about 10 ppm to about 3000 ppm, to thereby treat inflammation in the patient, wherein the patient inhales the gaseous composition.

15. A method of treating inflammation in a patient, comprising:
identifying a patient suffering from or at risk of inflammation of at least one organ selected from the group consisting of; kidney, spleen and skin; and administering to the patient a therapeutically effective amount of a gaseous composition comprising gaseous carbon monoxide at a concentration of about 10 ppm to about 3000 ppm, to thereby treat inflammation in the patient, wherein the patient inhales the gaseous composition.

16. A method of reducing inflammation secondary to sepsis in a patient, comprising:
identifying a patient suffering from or at risk of sepsis; and
administering to the patient a therapeutically effective amount of a gaseous composition comprising carbon monoxide at a concentration of about 10 ppm to about 3000 ppm, to thereby reduce inflammation secondary to sepsis, wherein the patient inhales the gaseous composition.

17. A method for reducing inflammation associated with a wound, the method comprising:
identifying a patient suffering from a wound; and
administering to the patient a therapeutically effective amount of a gaseous composition comprising carbon monoxide at a concentration of about 10 ppm to about 3000 ppm, wherein the amount is sufficient to reduce inflammation associated with the wound, wherein the patient inhales the gaseous composition.

18. A method of treating sepsis in a patient, comprising:
identifying a patient suffering from or at risk of sepsis; and
administering to the patient a therapeutically effective amount of a gaseous composition comprising carbon monoxide at a concentration of about 10 ppm to about 3000 ppm, to thereby treat sepsis in the patient wherein the patient inhales the gaseous composition.

19. A method of treating inflammation associated with arthritis in a patient, comprising:
identifying a patient suffering from or at risk for arthritis; and
administering to the patient a therapeutically effective amount of a gaseous composition comprising carbon monoxide at a concentration of about 10 ppm to about 3000 ppm, to thereby treat inflammation associated with arthritis in the patient, wherein the patient inhales the gaseous composition.

20. A method of treating a patient to reduce oxidative stress associated with hyperoxia, comprising:
identifying a human patient suffering from or at risk for oxidative stress associated with hyperoxia; and
administering to the patient a therapeutically effective amount of a gaseous composition comprising carbon monoxide at a concentration of about 10 ppm to about 3000 ppm, to thereby reduce oxidative stress associated with hyperoxia, wherein the patient inhales the gaseous composition.

21. The method of claim 20, wherein the composition comprises carbon monoxide at a concentration of at least 50 ppm.

22. The method of claim 20, wherein the composition comprises carbon monoxide at a concentration of at least 100 ppm.

23. The method of claim 20, wherein the composition comprises carbon monoxide at a concentration of at least 250 ppm.

24. The method of claim 20, wherein the composition contains carbon monoxide at a concentration of about 50 ppm to about 500 ppm.

25. A method of treating a patient to reduce hyperoxic lung injury, comprising:
identifying a human patient suffering from or at risk for hyperoxic lung injury; and
administering to the patient a therapeutically effective amount of a gaseous composition comprising carbon monoxide at a concentration of about 10 ppm to about 3000 ppm, to thereby reduce hyperoxic lung injury, wherein the patient inhales the gaseous composition.

26. The method of claim 25, wherein the composition comprises carbon monoxide at a concentration of at least 50 ppm.

27. The method of claim 25, wherein the composition comprises carbon monoxide at a concentration of at least 100 ppm.

28. The method of claim 25, wherein the composition comprises carbon monoxide at a concentration of at least 250 ppm.

29. The method of claim 25, wherein the composition contains carbon monoxide at a concentration of about 50 ppm to about 500 ppm.

30. A method of treating inflammation associated with Alzheimer's disease or Parkinson's disease, comprising:
identifying a patient suffering from or at risk for Alzheimer's disease or Parkinson's disease; and
administering to the patient a therapeutically effective amount of a gaseous composition comprising carbon monoxide at a concentration of about 10 ppm to about 3000 ppm, to thereby treat inflammation associated with Alzheimer's disease or Parkinson's disease, wherein the patient inhales the gaseous composition.

31. A method of treating inflammation in a patient, comprising:
identifying a patient suffering from inflammation of at least one organ selected from the group consisting of brain, spleen, and skin; and
administering to the patient a therapeutically effective amount of a gaseous composition comprising carbon monoxide at a concentration of about 10 ppm to about 3000 ppm, wherein the inflammation is of a type selected from the group consisting of acute, allergic, alternative, atrophic, catarrhal, croupous, fibrinopurulent, fibrinous, immune, hyperplastic, proliferative, subacute, serous and serofibrinous inflammation, wherein the patient inhales the gaseous composition.

32. A method of treating inflammation in a human patient, comprising:
identifying a patient suffering from inflammation of at least one organ selected from the group consisting of brain, spleen, and skin; and
administering to the patient a therapeutically effective amount of a gaseous composition comprising carbon monoxide at a concentration of about 10 ppm to about 3000 ppm, to thereby treat inflammation in the human patient, wherein the patient inhales the gaseous composition.

33. The method of claim 16, wherein the patient is a human.
34. The method of claim 17, wherein the patient is a human.
35. The method of claim 18, wherein the patient is a human.
36. The method of claim 19, wherein the patient is a human.
37. The method of claim 30, wherein the patient is a human.
38. The method of claim 31, wherein the patient is a human.
39. The method of claim 2, wherein the gaseous composition is a mixture comprising carbon monoxide, nitrogen and oxygen.
40. The method of claim 39, wherein the concentration of carbon monoxide in the mixture is monitored with a carbon monoxide analyzer.
41. The method of claim 2, wherein the patient is a human.

42. The method of claim 3, wherein the gaseous composition is a mixture comprising carbon monoxide, nitrogen and oxygen.

43. The method of claim 42, wherein the concentration of carbon monoxide in the mixture is monitored with a carbon monoxide analyzer.

44. The method of claim 3, wherein the patient is a human.

45. The method of claim 4, wherein the gaseous composition is a mixture comprising carbon monoxide, nitrogen and oxygen.

46. The method of claim 45, wherein the concentration of carbon monoxide in the mixture is monitored with a carbon monoxide analyzer.

47. The method of claim 4, wherein the patient is a human.

48. The method of claim 5, wherein the gaseous composition is a mixture comprising carbon monoxide, nitrogen and oxygen.

49. The method of claim 48, wherein the concentration of carbon monoxide in the mixture is monitored with a carbon monoxide analyzer.

50. The method of claim 5, wherein the patient is a human.

51. The method of claim 6, wherein the gaseous composition is a mixture comprising carbon monoxide, nitrogen and oxygen.

52. The method of claim 51, wherein the concentration of carbon monoxide in the mixture is monitored with a carbon monoxide analyzer.

53. The method of claim 6, wherein the patient is a human.

54. The method of claim 3, wherein the composition comprises carbon monoxide at a concentration of at least 50 ppm.

55. The method of claim 3, wherein the composition comprises carbon monoxide at a concentration of at least 100 ppm.

56. The method of claim 3, wherein the composition comprises carbon monoxide at a concentration of at least 250 ppm.

57. The method of claim 3, wherein the composition contains carbon monoxide at a concentration of about 50 ppm to about 500 ppm.

58. The method of claim 15, wherein the organ is kidney.

59. The method of claim 1, wherein the gaseous composition comprises carbon monoxide at a concentration of about 10 ppm to about 2500 ppm.

60. The method of claim 2, wherein the gaseous composition comprises carbon monoxide at a concentration of about 10 ppm to about 2500 ppm.

61. The method of claim 3, wherein the gaseous composition comprises carbon monoxide at a concentration of about 10 ppm to about 2500 ppm.

62. The method of claim 4, wherein the gaseous composition comprises carbon monoxide at a concentration of about 10 ppm to about 2500 ppm.

63. The method of claim 5, wherein the gaseous composition comprises carbon monoxide at a concentration of about 10 ppm to about 2500 ppm.

64. The method of claim 6, wherein the gaseous composition comprises carbon monoxide at a concentration of about 10 ppm to about 2500 ppm.

65. The method of claim 10, wherein the gaseous composition comprises carbon monoxide at a concentration of about 10 ppm to about 2500 ppm.

66. The method of claim 13, wherein the gaseous composition comprises carbon monoxide at a concentration of about 10 ppm to about 2500 ppm.

67. The method of claim 14, wherein the gaseous composition comprises carbon monoxide at a concentration of about 10 ppm to about 2500 ppm.

68. The method of claim 15, wherein the gaseous composition comprises carbon monoxide at a concentration of about 10 ppm to about 2500 ppm.

69. The method of claim 16, wherein the gaseous composition comprises carbon monoxide at a concentration of about 10 ppm to about 2500 ppm.

70. The method of claim 17, wherein the gaseous composition comprises carbon monoxide at a concentration of about 10 ppm to about 2500 ppm.

71. The method of claim 18, wherein the gaseous composition comprises carbon monoxide at a concentration of about 10 ppm to about 2500 ppm.

72. The method of claim 19, wherein the gaseous composition comprises carbon monoxide at a concentration of about 10 ppm to about 2500 ppm.

73. The method of claim 19, wherein the gaseous composition comprises carbon monoxide at a concentration of about 10 ppm to about 2500 ppm.

74. The method of claim 25, wherein the gaseous composition comprises carbon monoxide at a concentration of about 10 ppm to about 2500 ppm.

75. The method of claim 30, wherein the gaseous composition comprises carbon monoxide at a concentration of about 10 ppm to about 2500 ppm.

76. The method of claim 31, wherein the gaseous composition comprises carbon monoxide at a concentration of about 10 ppm to about 2500 ppm.

77. The method of claim 32, wherein the gaseous composition comprises carbon monoxide at a concentration of about 10 ppm to about 2500 ppm.

78. The method of claim 13, wherein the organ is kidney.

79. The method of claim 14, wherein the organ is kidney.

* * * * *

UNITED STATES PATENT AND TRADEMARK OFFICE
CERTIFICATE OF CORRECTION

PATENT NO. : 7,678,390 B2  Page 1 of 1
APPLICATION NO. : 10/053535
DATED : March 16, 2010
INVENTOR(S) : Augustine M. K. Choi et al.

It is certified that error appears in the above-identified patent and that said Letters Patent is hereby corrected as shown below:

Column 22, lines 12 and 46, replace "rpm" with --ppm--.

Column 22, lines 48-49, and column 24, line 39, replace "alternative," with --alterative,--.

Column 22, line 67, replace "of;" with --of:--.

Column 23, line 30, replace "patient" with --patient,--.

Column 26, line 34, replace "claim 19," with --claim 20,--.

Signed and Sealed this

Eighth Day of June, 2010

David J. Kappos
*Director of the United States Patent and Trademark Office*